United States Patent [19]
Dovey et al.

[11] Patent Number: 5,424,205
[45] Date of Patent: Jun. 13, 1995

[54] AMYLOIDIN PROTEASE AND USES THEREOF

[75] Inventors: Harry F. Dovey, Pacifica, Calif.;
Peter A. Seubert, San Mateo;
Sukanto Sinha, San Francisco, all of Calif.

[73] Assignees: Athena Neurosciences, Inc., So. San Francisco, Calif.; Eli Lilly and Company, Indianapolis, Ind.

[21] Appl. No.: 59,032

[22] Filed: May 7, 1993

Related U.S. Application Data

[60] Division of Ser. No. 766,351, Sep. 30, 1991, Pat. No. 5,292,652, which is a continuation-in-part of Ser. No. 594,122, Oct. 5, 1990, abandoned.

[51] Int. Cl.$^6$ ............................................. C12N 9/64
[52] U.S. Cl. ................................. 435/226; 435/219
[58] Field of Search ................................. 435/226, 219

[56] References Cited

U.S. PATENT DOCUMENTS

| | | | |
|---|---|---|---|
| 4,918,001 | 4/1990 | Kode | 435/24 |
| 5,200,339 | 4/1991 | Abraham | 435/212 |
| 5,252,463 | 10/1993 | Nelson et al. | 435/23 |

FOREIGN PATENT DOCUMENTS

| | | |
|---|---|---|
| 9200374 | 1/1992 | WIPO . |
| 9203542 | 3/1992 | WIPO . |

OTHER PUBLICATIONS

Abraham et al., (1990) Neurobiology of Aging 11:303.
Abraham et al., (1989) Soc. for Neuroscience Abstracts 15:648.
Woodbury et al., (1981) Methods in Enzymology 80:588–605.
Masters et al., (1985) Proc. Natl. Acad. Sci. USA 82:4245–4249.
Kang et al., (1987) Nature 325:733–736.
Ponte et al., (1988) Nature 331:525–527.
Kitaguchi et al., (1988) Nature 331:530–532.
Schechter et al., (1986) J. of Immunol. 137:962–970.
Nelson and Siman, (1990) J. of Biol. Chem. 265(7):3836–3843.
Esch et al., (1990), Science 248:1122–1124.
Oltersdorf et al., (1990) J. of Biol. Chem. 265(8):4492–4497.
Barrett, (1990) Biol. Chem. Hoppe–Seyler 371(Supp):3-11–320.
Orlowski et al., (1989) Biochem. J. 261:951–958.
Pierotti et al., (1990) Biochem. 29:10323–10329.
Abraham et al., (Jun. 1990) Am. Assoc. Neuropath., 66th Annual Meeting, Abstr. No. 217.
Abraham et al., Neurobiol. Aging 11:207.
Abraham et al., (1990) Peptide Res. 3(5):211.
Abraham et al., (Jan. 1991) Biochem. Biophys. Res. Commun. 174(2):790.
Abraham et al., (Apr. 1991) J. Cell Biochem. Supp. 15G:115, Abstract No. CH024.
Abraham et al., (Jul. 1991) J. Neurochem. 57, Supp: p. S109, Abstract Nos. D and 023.
Abraham, et al., (1992), Neuobiology of Aging, p. 576, Abst. 298.
Abraham, et al., (1992) Neurobiology of Aging, p. 580, Abst. 315.
Lehning, A. L., (1975) Biochemistry, Second Ed., Worth Pub., N.Y., p. 197.

*Primary Examiner*—Charles L. Patterson, Jr.
*Attorney, Agent, or Firm*—Jean M. Duvall

[57] ABSTRACT

A proteolytic enzyme isolated from human tissue which exhibits a proteolytic activity to hydrolyze Met-Asp peptide bond in an amyloid-like substrate is disclosed. This enzyme has been designated "amyloidin" because it proteolytically cleaves a Met-Asp bond similar to the one present in the amyloid precursor protein to release a fragment having the mature Asp terminus of the β-amyloid peptide. Antibodies to the amyloidin protease are also provided. Methods to isolate and purify the amyloidin protease are provided, as well as assays to screen for inhibitors of the amyloidin protease. Also disclosed is the gene encoding the protease and methods for expression of the protease by recombinant DNA means.

11 Claims, 4 Drawing Sheets

| 10B9 | 12H6 | 18B2 | 20G3 | 20G4 | 3G8 | 6F8 | 9C9 | 9D2 | 9G12 | RAB |
|------|------|------|------|------|-----|-----|-----|-----|------|-----|

AMYLOIDIN PROTEASE AND USES THEREOF

CROSS REFERENCE TO RELATED APPLICATIONS

This is a Division of application Ser. No. 07/766,351 filed Sep. 30, 1991, now U.S. Pat. No. 5,292,652, which is a continuation-in-part application of U.S. patent application Ser. No. 07/594,122 filed 5 Oct. 1990 now abandoned, the disclosure of which is specifically incorporated herein by reference.

FIELD OF THE INVENTION

The present invention relates to purification of mammalian enzymes and more particularly to the purification of human amyloidin protease, the identification of the gene encoding the protease, the identification of inhibitors of this protease, and various uses thereof.

BACKGROUND OF THE INVENTION

Proteases are enzymes possessing the activity of hydrolyzing peptide bonds in proteins and polypeptides. One subclass of proteases, the metalloproteases are dependent on an integral zinc atom catalysis and often require exogenous calcium for activity. One such enzyme, which has been referenced in the literature as collagenase-like peptidase (EC 3.4.99.31), Pz-peptidase (Barrett (1990) *Biol Chem Hoppe-Seyler* 371(Supp):3-11-320) or metalloendopeptidase (EC 3.4.24.15) (Orlowski, et al (1989) *Biochem J* 261:951-958) cleaves preferentially bonds on the carboxyl side of hydrophobic amino acid residues and is believed to function in the metabolism of bioactive peptides.

Similar enzymatic activity towards collagen sequence-based peptides have been detected in a number of human tissue extracts by various investigators; however, most of the work was confined to the measurement of peptidase activity using collagen sequence-based peptides (Lessley, et al (1985) *J Androl* 6(6):372-378; Rajabi, et al (1984) *Am J Obstet Gynecol* 150(7):821-826 and Ito, et al (1977) *Clin Chim Acta* 78(2):267-270 ). Pierotti, et al (1990) *Biochem* 29:10323-10329 recently report the molecular cloning and primary structure of rat testes metalloendopeptidase. The enzyme is composed of 645 amino acids with a molecular weight of 72,985 daltons. There does not appear to be any reports that provide identification of human Pz-peptidase, either by partial purification and characterization, or by using a battery of substrates or inhibitor profiles.

Recently, investigators have preliminarily identified a proteolytic activity from human brain of about 68,000 daltons that is capable of cleaving between the Met and Asp residues of a small synthetic peptide HSEVKM-DAEF, which corresponds to amino acids 592 through 600 in the β-amyloid precursor protein ("APP") (Abraham, et al (1990) *Neurobiol Aging* 11A:303) with an N-terminal His. When this peptide, having an $^{125}I$ radio-iodinated His residue, is incubated with "brain protease" fractions, fragments are generated and separated by thin layer chromatography (TLC). The N-terminal fragments were detected by exposure of the TLC plate to film (Abraham, et al (1991) *Biochem Biophys Res Comm.* 174: 790-796). The cleavage pattern obtained with the brain protease preparation was primarily at three sites, between the Lys-Met, Met-Asp, and Asp-Ala, with some cleavage obtained at His-Ser. The peptide cleavage was inhibited by diisopropylfluorophosphate (DFP), $\alpha_1$-antichymotrypsin, and protease nexin II, all of which only inhibit serine proteases. Based on chemical crosslinking studies with the iodinated peptide substrate, two bands, one at approximately 68,000 daltons and another at approximately 30,000 daltons, are suggested to be candidates for the protease(s) in the preparation.

In more recent presentations (Abraham, et al (1991) *J Cell Biochem Suppl.* 15G:115; Abraham, et al (1991) *J Neurochem* 57 (Suppl.):S109), these investigators claim at least two different proteases in the preparation, one being the previously described calcium-dependent serine protease, and the other a cysteine metalloprotease. To date, no structure or characterization or any of these proteases has been presented.

APP is a membrane-spanning glycoprotein that is expressed in many mammalian tissues and cell lines and is encoded by a gene that, in humans, is found on chromosome 21. The β-amyloid core protein, referred to as the β- or A4 peptide, is an approximately 39-42 amino acid long peptide fragment of APP, and is the major component of the myriad amyloid deposits that accumulate extracellularly in the brains of patients with Alzheimer's disease (AD) or form the cerebrovascular amyloid in associated blood vessels.

There are at least three forms of the precursor protein: APP695 (Kang, et al (1987) *Nature* 325:733); APP751 (Ponte, et al (1988) *Nature* 331:525); and APP770 (Kitaguchi, et al (1988) *Nature* 331:530) which refer to the number of amino acids in the primary protein transcript. All of these forms contain the β-peptide sequence, which starts 28 amino acids N-terminal to the beginning of the putative transmembrane region, and ends approximately 14 amino acids in the transmembrane region. The numbering of amino acids as used herein corresponds to that used for APP695.

Recent work on the metabolism of the APP in cell culture has clearly shown that after intracellular maturation of the full transmembrane form of the protein, there is a specific proteolytic processing event which leads to extracellular secretion of a large N-terminal region, and leaves behind in cell membranes a small, C-terminal fragment reactive with antisera to the carboxyl end of the APP (Oltersdorf, et al (1990) *J Biol Chem* 265:4492). The size of this C-terminally reactive fragment made it likely that it contains the entire β-peptide. However, characterization by direct protein sequencing of the N-terminal of this fragment showed that it starts at Leu17 of the β-amyloid core peptide where Asp597 of APP695 is counted as Asp1 of the β-peptide (Esch, et al (1990) *Science* 248:1122). Characterization of the soluble secreted form by isolation of the peptide containing its C-terminal region also clearly showed that it ends at Gln15. Thus, in this normal processing pathway, the transmembrane form of APP is cleaved inside the β-peptide (either before or after Lys16, which is missing; presumably, it is taken off either by a carboxypeptidase or an aminopeptidase activity post-cleavage), and thus this pathway precludes the formation or deposition of the β-peptide. It also follows then that an alternative proteolytic pathway must exist for generation of the β-peptide.

The most likely characteristic of such a pathway would be a proteolytic cleavage between Met596 and Asp597, since protein sequencing of either senile (core) or vascular amyloid always starts at this aspartic acid residue, although there has been reported to be a ragged N-terminus for core amyloid (Masters, et al (1985) *Proc Natl Acad Sci U.S.A.* 82:4245). The preliminary work reported by Abraham et al (1990) supra, provides some insight as to how APP might be proteolytically processed to release the β-amyloid core protein.

Identification of mammalian proteases that are capable of cleavage at this site is essential in order to screen for inhibitors of such cleavage. Such inhibitors would be useful for therapeutic intervention in AD.

Cell culture models of the blood brain barrier may be used for the design of drug delivery systems for the inhibitors of the present invention. Such cell culture models are disclosed in U.S. Pat. No. 90/05106, filed 13 Sep. 1990 and U.S. Pat. No. 90/05105, filed 13 Sep. 1990.

DISCLOSURE OF THE INVENTION

The present invention provides human amyloidin protease, capable of cleaving the Met-Asp peptide bond in the peptide N-acetyl-Ser-Glu-Val-Lys-Met-Asp-Ala-Glu-Phe-Arg (Seq ID No:1), substantially free of natural contaminants. The protease has an apparent molecular weight in the range of about 80,000 daltons as determined by SDS-polyacrylamide gel electrophoresis (under both reducing and non-reducing conditions).

Methods for the purification of amyloidin protease from human cells, including blood and brain tissue, are also provided. This protease may be used as a reagent in methods for the identification of inhibitors against this protease. Such methods include combining the protease with a putative inhibitor in the presence of an amyloid-like substrate under conditions sufficient to cleave the Met-Asp bond; and monitoring the reaction to see whether cleavage of the substrate has occurred.

As an additional aspect of the invention, the amyloidin protease can be used to raise antibodies, using either another species of animal, such as a rabbit, or a hybridoma cell line. The resulting antibodies are specific for the amyloidin protease and can be used in diagnostic tests such as, for example, an immunoassay, or in immunopurification methods.

Further, it has been found that antigenic potential resides in fragments of the whole amyloidin molecule. Thus, it is possible to raise antibodies that specifically recognize an immunogenic epitope of an amyloidin protease using a fragment of the polypeptide. The resulting antibodies can themselves be used for immunopurification of the respective protease or in diagnostic assays.

Also provided as an aspect of the invention is the gene encoding the human amyloidin protease, vectors containing the gene and host cells transformed with the gene which are capable of expressing human amyloidin protease.

BRIEF DESCRIPTION OF THE DRAWINGS

FIG. 4 is a Western blot analysis of a number of monoclonal antibodies against the amyloidin protease. RAB=rabbit polyclonal antisera.

MODES OF CARRYING OUT THE INVENTION

A. Definitions

Figure 1:
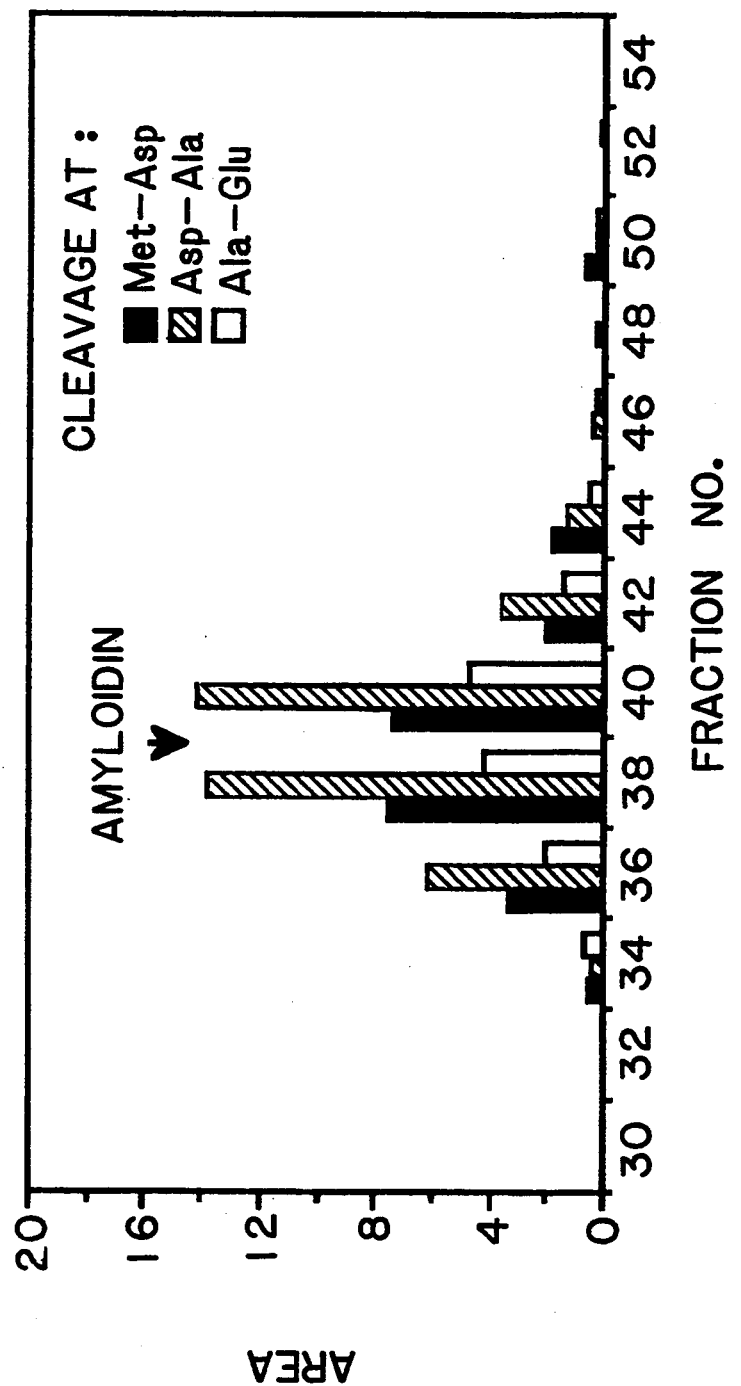
FIG. 1 is a chromatogram of amyloidin taken after the phenyl-TSK chromatography step. The characteristic three-site cleavage of N-acetyl-Ser-Glu-Val-Lys-Met-Asp-Ala-Glu-Phe-Arg (Seq ID No:1) by the eluted enzyme is shown.

"Amyloidin protease" or alternatively "amyloidin" as used herein refers to a native, human proteolytic enzyme which shares some homology to Pz-peptidase from other mammalian sources. The term also includes synthetic human amyloidin proteases, i.e., proteins produced by recombinant DNA means, direct chemical synthesis or a combination of both. Amyloidin protease is a polypeptide found, inter alia, in brain tissue and in blood.

The "amyloidin protease activity" of a protein refers to a peptide hydrolysis activity selective for a Met-Asp peptide bond similar to that found at the junction separating the β-amyloid core peptide from the amino-terminal region of APP. This activity can be assayed in vitro by incubating the amyloid protease with a synthetic substrate corresponding to the peptide sequence including the Met-Asp junction and determining the extent of cleavage. The amyloid protease activity predominantly cleaves the Met-Asp bond, although additional cleavage of certain amino-terminal β-amyloid core peptide residues is observed with at least one of the amyloid proteases of the invention. This multiple cleavage activity may contribute to the formation of the ragged amino-terminus of the β-amyloid core peptide originally observed by Masters, et al (1985), supra.

As used herein, "amyloid-like substrate" refers to an "amyloidogenic" polypeptide derived from the APP which has substantial homology to the region of the APP spanning the peptide sequence at the Met-Asp bond located at the amino-terminus of the β-amyloid core peptide. The source of the polypeptide includes, but is not limited to, microbially expressed APP or fragments thereof containing the Met-Asp cleavage site, endogenous APP present in biological materials such as cells or mammalian tissue homogenates, and synthetically produced peptides.

A peptide "derived from" a designated polypeptide sequence refers to a sequence which is comprised of a sequence of at least 6 amino acids, and preferably at least about 10-12 amino acids corresponding to a region of the designated polypeptide sequence. "Corresponding" means identical to or exhibiting a minimum of about 60% or more amino acid identity with the designated sequence. The derived sequence is not necessarily physically derived from the polypeptide sequence but may be generated in any manner, including chemical synthesis or DNA replication of the gene encoding the polypeptide and microbial expression thereof.

B. General Method

The practice of the present invention will employ, unless otherwise indicated, conventional techniques of protein purification, molecular biology, microbiology and recombinant DNA techniques, which are within the skill of the art. Such techniques are explained fully in the literature. See, e.g., "Guide to Protein Purification" in *Methods in Enzymology* (M. P. Deutscher, ed., (1990) Academic Press, Inc.); Sambrook, Fritsch & Maniatis, *Molecular Cloning; A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); *PCR Protocols, A*

*Guide to Methods and Applications* (M. A. Innis, et al, eds., (1990) Academic Press, Inc.); *Current Protocols in Molecular Biology* (F. M. Ausubel, et al, eds., (1989) John Wiley & Sons); and additional publications in the series, *Methods in Enzymology* (Academic Press, Inc.). All patents, patent applications, and publications mentioned herein, both supra and infra, are hereby incorporated by reference.

The present invention provides substantially purified human amyloidin protease free from natural contaminants. Purified amyloidin protease allows for the amino acid sequence to be determined, nucleic acid probes designed and amyloidin protease genes to be cloned. Once cloned, the amyloidin protease gene can be used to produce recombinant amyloidin protease.

The identity and characterization of human amyloidin protease further permits the development of in vitro screening models for agents which inhibit the cleavage of the Met-Asp bond in APP. If such cleavage inhibition is successful, β-amyloid core protein formation is prevented. Thus, this model provides a new and valuable medium with which to explore the molecular pathogenesis of amyloidosis relevant to AD and to evaluate potentially therapeutic agents.

As part of the initial work to identity proteases having proteolytic specificity for the Met-Asp peptide bond of APP, the following synthetic decapeptide was designed: N-acetyl-Ser-Glu-Val-Lys-Met-Asp-Ala-Glu-Phe-Arg. The C-terminal end can be either a free carboxylate (COOH) or an amide (CO-NH$_2$).

This peptide spans the putative Met-Asp cleavage site and is referred to herein as APP592-601. In addition to this substrate, other amyloid-like substrates may be employed in an inhibition assay to screen for protease activities isolated from mammalian sources which are capable of cleaving the Met-Asp peptide bond in this sequence. As taught in the examples, amyloid-like substrates also may be used to characterize the substrate specificity of the amyloid proteases described in the present invention. While endopeptidic cleavage predominates at the Met-Asp bond, cleavage may also occur at the Asp-Ala and Ala-Glu bonds of the β-peptide. Endopeptidic cleavage of the amyloid-like substrate is detected by reverse phase high performance liquid chromatography (HPLC), and the site of cleavage determined by amino acid analysis of the peptide fragments.

To isolate the amyloid protease activities of the present invention, extracts of mammalian tissues were made in a variety of aqueous buffers, such as, for example, Tris, phosphate and HEPES, of about 20–50 mM pH 7.5, at 4°–8° C., using conventional homogenation procedures, such as, for example, Waring blender or Teflon homogenizer, followed by repeated centrifugation at 10,000–15,000×g. The supernatant soluble fraction from this stage ("low ionic strength") are decanted and the pellet is further extracted with high ionic strength salt, for example 1M NaCl, and a detergent, such as 1% Triton X-100. If, however, the amyloidin proteases are to be isolated from mammalian cells such as erythrocytes, conventional cell disruption techniques may be employed. Such techniques include homogenization, sonication, osmotic lysis and pressure cycling. Prior to disruption, the cells may be first concentrated by filtration, centrifugation, or other conventional methods.

The various extracts are generally incubated with the amyloid-like substrates under a variety of conditions. For an initial screen, about 25 ul of the extract are incubated with 10 ul of a 2 mg/ml solution of the amyloid-like substrate, along with 10 ul of 1M Tris-HCl, pH 7.5, and 5 ul of a solution of water, or 10 to 100 mM CaCl$_2$ or 10 to 100 mM EDTA. After a 30–60 min incubation of the reaction mixture in a water bath at 37° C., the reactions are quenched by addition of multiple volumes of ice-cold ethanol, placed in ice for about 20 min and the samples are centrifuged at 15,000×g for 10 min in an Eppendorf microfuge. The supernatant is removed, dried under vacuum evaporation and reconstituted with water.

Aliquots of the sample are analyzed by injection onto a C18 reversed-phase HPLC column and elution with a 0–60% gradient of 0.1% TFA/acetonitrile, to assess the degradation of the substrate. Multiple fragments were produced when the peptide was incubated in the presence of from 0.1 to 10 mM Ca$^{++}$ ions at a pH range over 6.5 to 8, with soluble fractions obtained from low-ionic strength extracts. Little peptide cleavage activity was detected under other extraction conditions, for example, with high salt or detergents. Analysis of the peptide fragments produced by quantitative amino acid analysis indicated that the major sites of cleavage were between the Met-Asp, the Asp-Ala, and the Ala-Glu bonds. The Met-Asp cleaving activity from the crude extract was isolated for further purification.

The purification methods referred to herein include a variety of procedures. Among several types which may be useful are size fractionation using molecular sieve chromatography; ion exchange chromatography under suitable conditions; adsorption chromatography using nonspecific supports, such as hydroxyapatite, silica, alumina, and so forth; dye-ligand interaction chromatography, such as Cibacron Blue F3GA-Sepharose, Chromatofocusing ®; and also gel-supported electrophoresis. In the case of the amyloidin protease, hydrophobic interaction chromatography, such as using phenyl-Sepharose, phenyl-Superose or phenyl-TSK, has been shown to be particularly useful to separate the amyloid protease activity from natural contaminants including an activity which, while not consistently reproducible, shares the Met-Asp cleavage activity. Hydrophobic interaction chromatography also serves to provide substantial purification. This procedure separates proteins based on the hydrophobic properties of the protein, unlike ion exchange chromatography which separates based on charge properties of the protein.

In addition, initial purification of the proteases using ion exchange chromatography (such as with using weak anion exchangers, for example, DEAE-Sepharose) has been shown to be a particularly effective procedure to increase the purity of the amyloidin protease. While the ion exchange chromatography process is described herein primarily with respect to a cross-linked cellulose having functional diethylaminoethyl moieties and sold, for example, under the trademark DE52 (Whatman), other resins, particularly other mildly anionic resins, are suitable for partially purifying amyloidin protease-containing extracts by ion exchange chromatography. Other suitable resins include but are not limited to cross-linked dextran having DEAE moieties, and polystyrene cross-linked with benzene having polyaminoethylene moieties. When the amyloidin protease is being prepared bacterially or in some other culture, as will be possible using recombinant DNA procedures, pre-purification steps may be omitted.

Each of these purification techniques are, in a general sense, well known in the art, and a detailed description of the peculiarities of their specific application to the amyloidin protease is described in the examples below.

During the isolation steps, purification of the amyloidin protease is monitored by testing chromatography fractions for its ability to cleave the Met-Asp peptide bond in an amyloid-like substrate as analyzed by RP-HPLC.

Amyloidin has multiple cleavage sites, although the predominant cleavage site occurs at the Met-Asp peptide bond. Replacement of amino acid residues at the amino-terminal region of the amyloid-like substrate can eliminate or reduce cleavage at the additional sites as shown in Example 5 herein.

Once substantially purified, the native amyloidin protease may also be subjected to amino acid sequence analysis. Applying conventional peptide sequencing procedures, using for example, an Applied Biosystems model 470A gas-phase sequencer amino acid sequences for the amyloidin protease may be generated.

The amino acid composition of amyloidin is as follows:

| Residue | Predicted Composition* |
| --- | --- |
| Asx | 58.6 |
| Glx | 94.2 |
| Ser | 31.7 |
| Gly | 51.7 |
| His | 23.6 |
| Arg | 61.0 |
| Thr | 32.8 |
| Ala | 57.1 |
| Pro | 29.1 |
| Tyr | 26.0 |
| Val | 43.1 |
| Met | 16.3 |
| Cys | 8.6 |
| Ile | 18.7 |
| Leu | 83.3 |
| Phe | 30.0 |
| Trp | ND |
| Lys | 44.1 |

*Predicted Composition equals the number of approximate amino acids; Asx and Glx refer to (Asp and Asn) and (Glu and Gln), respectively; Cys was not quantitatively determined; Trp was not determined.

The purified amyloidin protease can be used to raise either polyclonal or monoclonal antibodies. The amyloidin protease is injected into a mammal, such as rabbits, mice or guinea pigs, and the resulting antibodies recovered from the serum. Alternatively, monoclonal antibodies may be produced by immunization of mice with either the purified protein or fragments thereof, and fusion of their splenic cells with murine myeloma or plasmacytoma cells. These protocols are conventional in the art.

One of the internal peptides of amyloidin has been shown to be immunogenic. This sequence, as well as other immunogenic regions, may be produced synthetically using available amino acid synthesizers. Such immunogenic peptides contain epitopes, that is, a determinant responsible for specific interaction with an antibody molecule.

Antibodies to either the whole amyloidin protease or to immunogenic fragments derived therefrom can be used in standardized immunoassays, such as radioimmunoassays (RIA) and enzyme-linked immunosorbent assays (ELISA). In addition, such antibodies may be used to localize the protease in immunochemical or immunohistochemical methods, as further described in the examples.

Once the amino acid sequence is determined, recombinant DNA encoding the amyloidin protease may be prepared. First, oligonucleotide probes encoding a portion of the determined amino acid sequence are prepared and used to screen DNA libraries for the gene encoding the amyloidin protease. The basic strategies for preparing oligonucleotide probes and DNA libraries, as well as their screening by nucleic acid hybridization, are well known to those of ordinary skill in the art. See, for example, *DNA Cloning: Volume I* (D. M. Glover, ed. 1985); *Nucleic Acid Hybridization*, supra; *Current Protocols in Molecular Biology*, supra; and *Molecular Cloning: A Laboratory Manual*, supra.

First, a DNA library is prepared. The library can consist of a genomic DNA library from a selected mammal, such as human. DNA libraries can also be constructed of cDNA prepared from a poly-A RNA (mRNA) fraction by reverse transcription. The mRNA is isolated from a cell line or tissue known to express the amyloidin protease. cDNA (or genomic DNA) is cloned into a vector suitable for construction of a library. A preferred vector is a bacteriophage vector, such as phage lambda. The construction of an appropriate library is within the skill of the art. Alternatively, the cDNA or genomic library may also be purchased from commercial sources, for example, Clontech and Stratagene, Inc.

Once the library is obtained, oligonucleotides to probe the library are prepared and used to isolate the desired amyloidin gene. The particular nucleotide sequences selected are chosen so as to correspond to the codons encoding a known amino acid sequence from the amyloidin protease. Since the genetic code is redundant, it will often be necessary to synthesize several oligonucleotides to cover all, or a reasonable number, of the possible nucleotide sequences which encode a particular region of the protein. One can also design a single probe or "guessmer" wherein one uses codon bias and other considerations, such as CG dinucleotide underrepresentations to guess the best sequence, or by using inosine bases where ambiguity in the sequence exists (Sambrook, et al, supra). It may also be desirable to use two probes (or sets of probes), each to different regions of the gene, in a single hybridization experiment. Automated oligonucleotide synthesis has made the preparation of probes relatively straightforward. In addition, probes may be commercially obtained.

Alternatively, one may use the polymerase chain reaction (PCR) to amplify a portion of the desired gene encoding the amyloidin protease. In its simplest form, PCR is an in vitro method for the enzymatic synthesis and amplification of specific DNA sequences, using two oligonucleotide primers that hybridize to opposite strands and flank the region of interest in the target DNA. A repetitive series of cycles involving template denaturation, primer annealing, and the extension of the annealed primers by DNA polymerase results in the exponential accumulation of a specific fragment whose termini are defined by the 5' ends of the primers. PCR reportedly is capable of producing a selective enrichment of a specific DNA sequence by a factor of $10^9$. The PCR method is described in Saiki, et al (1985) *Science* 230:1350 and is the subject of U.S. Pat. Nos. 4,683,195, 4,683,202 and 4,800,159. The portion of the amyloidin gene synthesized by the PCR technique will be used to probe cDNA libraries for clones encoding the full length amyloidin cDNA.

Because the genetic code is redundant, PCR from known amino acid sequence requires PCR with either degenerate, inosine substituted, or "guessmer" PCR oligos. (See PCR Protocols, Innis, et al, supra, especially the chapter on "Degenerate Primers for DNA Amplification" at pp. 39–45; Sambrook, et al, supra; Maisonpiere, et al (1990), *Science* 247:1446; Hohn, et al (1990) *Nature* 344:339. These techniques have been widely used to clone a variety of genes as described in the above references. One can use PCR to amplify DNA sequences from either cDNA generated from RNA, genomic DNA or from a cDNA or genomic library. Strategies using either conventional PCR as described above, or "anchor" PCR could be used. In anchor PCR, one uses a library containing the amyloidin gene as the PCR substrate, and uses one sequence within the amyloidin gene and another within the vector that the library is in so that the region amplified contains sequences from the vector as well as from the amyloidin gene. In this case only very limited amino acid information is necessary. PCR conditions and components such as temperatures, concentrations of magnesium, Taq polymerase, and oligos would be optimized as described in Innis, et al, supra. One might also utilize conditions where 7-deazaguanine is used to allow the amplification of sequences containing secondary structure.

As an alternative to cloning the gene based on nucleic acid probes, one can use the amino acid sequence of amyloidin to prepare antibody probes that can be used to screen for the amyloidin gene. Given the amino acid sequence, peptides of identical sequence can by synthesized by standard techniques, and these peptides can be used to immunize rabbits or mice. Polyclonal or monoclonal antibodies to either amyloidin or peptides derived therefrom can be generated and used to detect amyloidin clones from an appropriate library. Libraries made in vectors which are designed to express the gene of interest, include but not limited to lambda gtll, lambdaZAP, or lambdaORF8 (see Ausubel, et al, supra, and Sambrook, et al, supra) can be screened with an antibody to that library. Libraries in these vectors can be generated or purchased from sources such as Clontech or Stratagene. The protein of the cloned gene is expressed in these vectors and the ability of an antibody to bind to the expressed protein allows one to identify the amyloidin clone by standard antibody probing techniques.

A DNA molecule containing the coding sequence for amyloidin protease can be cloned in any suitable vector and thereby maintained in a composition substantially free of vectors that contain the coding sequence of other mammalian genes, including those encoding other amyloidin protease activities. Numerous cloning vectors are known to those of skill in the art, and the selection of an appropriate cloning vector is a matter of choice.

For expression of the amyloidin protease, a variety of systems can be used, including, but not limited to, bacterial, yeast, insect, and mammalian systems.

Bacterial expression vectors such as pEx12Mcr and pEx10mer (Seedorf, et al (1987) *EMBO J* 6:139) and a variety of vectors discussed in the above cited publications, can be used to express fusion proteins that contain amyloidin sequences linked to bacterial genes. Other bacterial expression vectors can be used to make intact full-length amyloidin in bacterial cells. For bacterial expression the vector needs to have a bacterial promoter and a ribosome binding site.

Mammalian vectors useful in the present invention include, but are not limited to pORFex13 (Bernard, et al (1987) *EMBO J* 6:133), pL1, pcDV1, pcD-X (all from Okayama and Berg (1983) *Mol Cell Biol* 3:280), pSV2 and derivatives thereof including pSVneo and pSVdhfr (Sambrook, et al, supra), pRSVneo (Gorman, et al (1983) *Science* 221:551 and vectors derived from these and/or related vectors such as pRSVcat (Gorman, et al (1982) *Proc Natl Acad Sci U.S.A.* 79:6777) can be used to express amyloidin in a variety of mammalian cell types. The amyloidin gene is placed in these vectors in operable juxtaposition and then put into animal cells by standard techniques. Once inside the cell the protein is expressed from these vectors containing the amyloidin gene. Such expression control elements for expression in animal cells include a promoter, enhancer, splice site (this is optional) and polyadenylation sequences. A variety of systems are available for expression in animal virus systems, such as, for example, bovine papiloma virus, retroviruses, SV40 and other viruses as described in Ausubel, et al, supra and Sambrook, et al, supra, and in "High Level Production of Proteins in Mammalian Cells" by Randal J. Kaufman, in *Genetic Engineering* (1987) vol 9:155–198, Jane K. Stelow, ed.

The insect virus system based on baculovirus vectors can also be used to express the amyloidin gene. Insect virus systems are commercially available from Invitrogen Corp., San Diego, Calif. Such vectors include, but are not limited to pac373 ("A Manual for Methods for Baculovirus Vectors and Insect Cell Culture Procedures" by Max Summers and Gale Smith, published by Texas Agricultural Experiment Station), pVL941 (Luckow and Summers, (1989) *Virology* 170:31). These vectors can be used to transfer the amyloidin gene into a baculovirus and the recombinant virus thus obtained used to infect insect cells. The infected insect cells are used to produce amyloidin protein. Complete methods for these procedures are described in Summers, et al, supra.

The amyloidin protease of the present invention can be used to develop and/or identify agents which inhibit the cleavage of the Met-Asp bond similar to that found in APP. The selection of appropriate inhibitor molecules will generally be guided by the rate at which the test compound inhibits cleavage of the amyloid-like substrate. Inhibition assays may be developed to assess the inhibitory spectrum of various test compounds on the cleavage of the amyloid-like substrate in the presence of the amyloidin protease.

A suitably modified amyloid-like substrate may be incubated, under conditions of neutral pH in a suitable aqueous buffer, with a protease that has been incubated with a potential inhibitory compound (at room temperature for 15–30 min, for example), for 1–4 hr, or a period of time sufficient to obtain significant endopeptidic cleavage of the substrate in the absence of the inhibitory agent. The proportion of cleavage is then quantitated. Suitably varying the concentration of the inhibitor compound and measuring the inhibition of cleavage as compared to zero inhibitor concentration, will allow one to determine an inhibition curve, from which the inhibitory efficacy, such as the inhibitor concentration at which 50% of the enzyme's cleavage activity is inhibited, or the inhibition constant ($K_i$) can be calculated by standard methods.

The present invention also provides the discovery that "clipsin", a chymotrypsin-like protease, selectively cleaves the amyloid substrate APP592–601 at the Met-Asp peptide bond. Clipsin was first reported by Nelson and Siman (1990) *J Biol Chem* 265:3836, and was partially purified from rat brain. These investigators showed that clipsin was relatively specific for the APP, but they did not identify any specific cleavage site. Also reported was the specificity of additional known proteins, such as calpain, for APP.

As shown herein, selectivity for the Met-Asp peptide bond persists even when clipsin is subjected to a further purification step (chromatography on a soybean trypsin inhibitor affinity column). These data are not obvious in view of the strong Suc-Ala-Ala-Pro-Phe-pNa ($K_{cat}/K_m=57,000$) and weak Suc-Ala-Ala-Pro-Met-pNA ($K_{cat}/K_m=5,200$) cleavage activity of clipsin previously reported. While the Nelson and Siman paper dismissed the possibility that clipsin might be one of the identified rat mast cell proteases, RMCP I and II (Woodbury, et al (1981) *Methods in Enzymol* 80:588), comparison of the enzymatic properties of clipsin with authentic RMCP I and with human skin chymase (the analogous human mast cell enzyme disclosed in Schechter, et al (1986) *J Immunol* 137:962) using the amyloid-like substrate APP592–601, clearly showed that all three proteases cleaved the APP592–601 peptide at the Met-Asp bond. Nelson, et al (1990) *Soc Neuroscience Abstr* 16:788) have recently reported more complete purification of "clipsin", including the partial amino acid sequence from the N-terminus, which indicate that clipsin indeed is RMCP I.

RMCP I, RMCP II and human skin chymase are known to belong to a family of related chymotrypsin-like proteases, also called "chymases." Members of this family include, for example, mouse mast cell proteases 1–6 (Reynolds, et al (1990) *Proc Natl Acad Sci U.S.A.* 87:3230–3234) and possibly, human cathepsin G. Each of these mammalian proteases which exhibit the Met-Asp cleavage activity may be considered equivalents for purposes of testing inhibitory agents of the amyloidin protease of the present invention.

For analysis of cleavage inhibition, the amyloid-like substrate may be labeled, as described below, by incorporating moieties detectable by spectroscopic, photochemical, biochemical, immunochemical, or chemical means. The method of linking or conjugating the label to the amyloid-like substrate depends, of course, on the type of label(s) used and the position of the label on the substrate.

A variety of labels which would be appropriate for use in the invention, as well as methods for their inclusion in the substrate, are known in the art and include, but are not limited to, enzymes (e.g., alkaline phosphatase and horseradish peroxidase (HRP)) and enzyme substrates, radioactive atoms, fluorescent dyes, chromophores, chemiluminescent labels, ligands having specific binding partners, or any other labels that may interact with each other to enhance, alter, or diminish a signal.

"Specific binding partner" refers to a protein capable of binding a ligand molecule with high specificity, as for example in the case of an antigen and a monoclonal antibody specific therefor. These types of binding partners are also referred to in the art as "capture" labels. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a monoclonal antibody.

Further, one may combine various labels for a desired effect. In some situations it may be desirable to use two labels on a single substrate with due consideration given for maintaining an appropriate spacing of the labels to permit the separation of the labels during hydrolysis of the peptide bond. For example, one might label a substrate at its N-terminus with biotin and its C-terminus with a radioactive label. One would detect cleavage of the substrate by passing the reaction mixture over or through a solid phase extractant (SPE) containing avidin or streptavidin. The SPE is monitored to assess whether the signal of the C-terminal label changes. Any decrease in signal intensity is an indication of cleavage inhibition. Other permutations and possibilities will be readily apparent to those of ordinary skill in the art, and are considered as equivalents within the scope of the instant invention.

C. Examples

The examples presented below are intended to be illustrative of the various methods and compositions of the invention.

EXAMPLES

Example 1

Purification Scheme

A. Protein Purification from Brain Tissue

Frozen human brain tissue (500 g wet weight) was thawed, then homogenized in a Waring blender with three parts (v/w) of ice-cold 20 mM Tris, pH 7.5, 2 mM EDTA, 5 mM 2-mercaptoethanol ("Buffer A"). The mixture was centrifuged at 10,000×g for 60 min at 4° C., and the pellet discarded. The supernatant was recentrifuged at 15,000×g for 60 min.

About 1 l of the centrifuged solution was applied to a 100 ml packed DE-52 diethylaminoethyl anion exchange column pre-equilibrated with Buffer A. After loading for 8 hr at 4° C., the column was washed with 10 volumes of 1 l of Buffer A, then eluted with 60 mM NaCl in Buffer A. Fractions of the eluate containing peptide cleavage activities were pooled and concentrated in an Amicon pressure cell to 5 ml.

The concentrated eluate was chromatographed on a 2.5×100 cm S-200 Sephacryl (Pharmacia) molecular sieving column, equilibrated with Buffer A supplemented with 100 mM NaCl, and chromatographed overnight at 4° C. at 1 ml/min. All three peptide cleavage activities eluted in a symmetrical peak with an apparent MW of 80,000. The fractions containing peptide cleaving activity were pooled, then dialyzed for 16 hr at 4° C. into 10 mM sodium phosphate, pH 7.5, containing 10 uM $Ca^{++}$.

The dialyzate was then loaded on to a Bio-Gel HT column (Bio-Rad) (40 ml bed volume) pre-equilibrated with the same buffer used for dialysis at 1 ml/min at 4° C., washed with five volumes of the buffer, and then eluted with a 250 ml 10 to 250 mM sodium phosphate linear gradient. The protease activity eluted at approximately 100 mM sodium phosphate. The sharp peak of activity was pooled, made 1M in ammonium sulfate (by dilution with 3M ammonium sulfate in 100 mM sodium phosphate, pH 7.5) centrifuged at 15,000×g at 4° C. for 20 min, and the supernatant loaded at 4° C. onto a 7.5×75 mm HPLC Phenyl-TSK column equilibrated in 1M ammonium sulfate in 100 mM sodium phosphate, pH 7.5. The column was washed with 10 ml of the equilibration buffer, and eluted using a linear gradient in which the ammonium sulfate concentration decreased from 1M to 0M. The amyloidin fractions eluted at approximately 0.4M ammonium sulfate and were pooled.

The purification steps described here are important, since at least one major contaminating protease activity is separated out at the Phenyl-TSK step. This activity, which is not affected by $Ca^{++}$, and cleaves the peptide at the Ala-Glu bond, elutes early from the column, followed by the characteristic three-site cleavage pattern of amyloidin. The chromatogram shown in FIG. 1 and developed from the material eluted from the Phenyl-TSK HPLC column, shows the characteristic three-site cleavage by amyloidin. Although we were able to detect an activity which we designated "amyloidin II" that also cleaved the substrate at the Met-Asp bond, this activity could not be reproducibly isolated.

The pooled material was dialyzed at 4° C. for 4 hr against 25 mM bis-Tris, pH 6.3 and then applied to a 1.5×30 cm PBE 94 Chromatofocusing ® column (Pharmacia) pre-equilibrated with the 25 mM bis-Tris, pH 6.3 buffer. The column was eluted with a decreasing pH gradient from 6.3 to 3.8 using Polybuffer 74 diluted ⅛ with water, and adjusted to pH 3.8 with HCl. Amyloidin fractions eluted at an approximate pH of 4.3. SDS-PAGE (reducing conditions) analysis of fractions containing amyloidin activity showed a predominant band at 80,000, as estimated by the relative mobility against low molecular weight protein markers purchased from Bio-Rad (Richmond, Calif.).

B. Protein Purification of Amyloidin from Blood

Outdated blood was obtained from the blood bank. Six units of whole blood were centrifuged at 2,000×g for 30 min, and the plasma and buffy coat discarded. The packed cells were washed four times with Buffer A plus 140 mM NaCl, with centrifugation at 2,000×g for 30 min and discarding the wash after each step. The collected, washed erythrocytes were lysed by osmotic shock in 6 volumes of 5 mM Tris-HCl, pH 7.5, 2 mM EDTA and 5 mM 2-mercaptoethanol, for 30 min on ice, then centrifuged at 15,000×g for 60 min at 4° C.

The supernatant was mixed with DE-52 (Whatman) pre-equilibrated with Buffer A using approximately 85 ml of settled bed volume for the ion exchanger per unit of whole blood. The DE-52 slurry was stirred for 1 h on ice, then washed in a Buchner funnel with 8 L of the Buffer A solution. The washed ion exchanger was packed into a glass column, washed with 4 L of Buffer A, then eluted with 60 mM NaCl in Buffer A.

The pool of peptide-cleavage activity was dialyzed against 4 L of 10 mM sodium phosphate, pH 7.5, 10 uM $CaCl_2$, and the dialyzate passed through an Affigel Blue column (50 ml bed volume, Bio-Rad). All the peptide cleavage activity passed through the column unretarded. The solution was collected and loaded onto a 100 ml Bio-Gel HT column pre-equilibrated with the dialyzing buffer. The column was then washed with 100 ml of the same buffer and eluted with a linear gradient of 10–250 mM sodium phosphate, pH 7.5, 10 uM $CaCl_2$, total volume 600 ml. The peak of peptide cleavage activity was pooled, then dialyzed against 25 mM Bis-Tris, pH 6.3, and applied to a 1.5×40 cm PBE 94 (Pharmacia) Chromatofocusing ® column.

The Chromatofocusing ® column was washed with 200 ml of the loading buffer and the retentant eluted with a decreasing pH gradient from 6.3 to 3.8, using Polybuffer 74 diluted 1:8 with water and then the pH was adjusted to 3.8 with HCl. The amyloidin activity (eluting at approximately pH 4.3) was pooled, and then dialyzed against 100 mM sodium phosphate, pH 7.5, 1M ammonium sulfate. The dialyzate was then loaded onto a 7.5 mm×75 mm HPLC Phenyl-TSK column (Toyo-Soda, Japan) equilibrated with the dialysis buffer, washed with 10 ml of the equilibration buffer, then eluted using a linear gradient in which the ammonium sulfate concentration decreased from 1M to 0M. The amyloidin fractions eluted at approximately 0.4M ammonium sulfate and were pooled.

C. Alternative Protein Purification Scheme

Following initial tissue extration procedures as described for brain tissue (1A) or blood (1B) above, the soluble extract was mixed with DE-52 (Whatman) pre-equilibrated with 20 mM Tris, pH 7.5, 2 mM EDTA, 5 mM β-mercaptoethanol, using approximately 100 ml packed resin per liter of extract.

Peptide cleavage activity was pooled and dialyzed against 4 l of 10 mM sodium phosphate, pH 7.5, 10 μM $CaCl_2$, then applied to a 100 ml Bio-Gel HT column pre-equilibrated with the dialyzing buffer. The elution of this column and subsequent steps, e.g., PBE 94 (Pharmacia) Chromatofocusing ® and HPLC phenyl-TSK chromatography, were done exactly as described in Example 1B above. The exact order of these subsequent steps may be performed in a different sequence than that presented in this example. When phenyl-TSK chromatography preceded PBE 94 Chromatofocusing ®, similar purification and yields were obtained.

| Fraction | Volume (ml) | (Protein) (mg/ml) | Total Protein (mg) | Total Activity DAEFR area, mV-sec/min) | % Yield | Specific Activity (area/min/mg protein) | Fold Purification |
| --- | --- | --- | --- | --- | --- | --- | --- |
| Crude | 4200 | 236 | 991200 | 114371 | 100.00% | 0.12 | 1 |
| DE52 | 165 | 10.1 | 1666.5 | 422334 | 369.27% | 253.43 | 2196 |
| HT | 142 | 1.4 | 198.8 | 59252 | 51.81% | 298.05 | 2583 |
| PBE 94 | 150 | 0.54 | 81 | 62125 | 54.32% | 766.98 | 6647 |
| Phe TSK | 40 | 0.14 | 5.6 | 11644 | 10.18% | 2079.29 | 18020 |

D. Enzymatic Assay

The peptides of the invention can be prepared by solid phase synthesis (Kent and Lewis in "Synthetic Peptides in Biology and Medicine," Alitalo, ed. (1985) Elsevier) or by other standard peptide synthetic means. APP592–601 was synthesized by Applied Biosystems (Foster City, Calif.) and the anhydrous hydrogen fluoride (HF)-crude further purified by reverse-phase HPLC. The composition was confirmed by amino acid analysis on an Applied Biosystems 420 Automated Amino Acid Analyzer. APP592–601 has a free carboxy terminus which is preferred for purposes of the cleavage assay described below, whereas the analogs synthesized below have a C-terminal amide.

Routinely, 25 ul of enzyme solution were mixed with 10 ul of 1M Tris, pH 7.5, 5 ul 10 mM $CaCl_2$, and 10 ul of a 2 mg/ml Stock solution of APP592-601 in water, or 20 mM Tris, pH 7.5, 0.15M NaCl, in 1.5 ml polypropylene microfuge tubes. The reaction mixtures were incubated for 60 min at 37° C. in a water bath, then quenched with 450 ul ice-cold ethanol, and incubated on ice for a further 20 min. They were centrifuged at 15,000×g for 10 min, and the supernatants transferred to new polypropylene tubes and dried under vacuum. The residue was dissolved in 0.5 ml water, centrifuged at 15,000×g for 5 min, and 200 ul of the supernatant injected onto a 0.46×30 cm Vydac C18 column equilibrated with 0.1% trifluoroacetic acid in water, at 1 ml/min. The column was immediately eluted with a linear gradient to 40% acetonitrile in 0.1% trifluoroacetic acid in water, over 20 minutes. The elution was monitored at 220 nm, and peaks were individually collected, hydrolyzed in 6N HCl at 65° C. for 2 hr, then subjected to quantitative amino-acid analysis in an Applied Biosystems amino-acid analyzer. Once identified, times of elution were used to identify cleavage patterns. The characteristic three-site cleavage pattern of amyloidin is shown in FIG. 1.

Example 2

Enzymatic Properties

Amyloidin is strongly inhibited by EDTA, since substitution of 5 ul 100 mM EDTA for the $CaCl_2$ in the standard peptide cleavage assay described in Example 1D, leads to no detectable cleavage of the APP592-601 by this protein.

Figure 2:
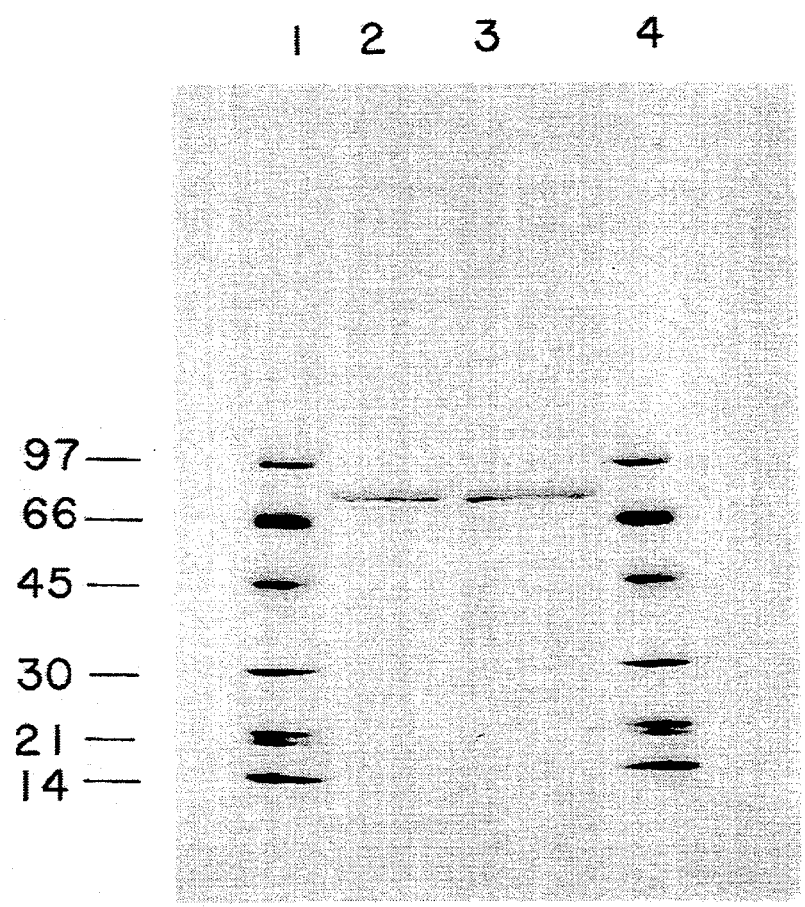
FIG. 2 is a Coomassie-stained gel of purified amyloidin.

The molecular weight estimate for the purified amyloidin was made by comparing the mobility of the Coomassie-stained band with that of low molecular weight standard protein markers (FIG. 2, Lanes 1 and 4) supplied by Bio-Rad (phosphorylase B, 97,400; bovine serum albumin, 66,200; ovalbumin, 42,700; carbonic anhydrase, 31,000; soybean trypsin inhibitor, 21,500; and lysozyme, 14,400); Lane 2 is amyloidin (non-reducing); and Lane 3 is amyloidin (reducing).

The inhibition of amyloidin by various inhibitors was tested by individually pre-incubating the enzyme with the inhibitor compounds listed in the following table for 30 min at room temperature, prior to addition of APP5-92-601 to start the reaction. The conditions for each reaction are also provided in the table. The solvent stock solution of inhibitor is made up in water unless otherwise indicated (DMSO, dimethylsufoxide; EtOH, ethanol). Percent of activity of amyloidin is shown, as calculated with respect to control without inhibitor but with appropriate solvent.

| Inhibition of Amyloidin | | | |
|---|---|---|---|
| Inhibitor* | Stock conc. | Assay conc. | % Control Activity |
| PMSF | 50 mM EtOH | 1 mM | 69 |
| DFP | 20 mM EtOH | 2.5 mM | 0 |
| EDTA | 100 mM | 10 mM | 0 |
| E-64 | 10 ug/ml | 1 ug/ml | 119 |
| 1,10-phen. | 5 mM DMSO | 0.1 mM | 75 |
| phosphoramidon | 1 mg/ml | 0.1 mg/ml | 79 |
| Calp. Inh. II | 2.5 mg/ml | 50 ug/ml | 130 |
| chymostatin | 1 mg/ml DMSO | 25 ug/ml | 77 |
| aprotinin | 0.1 mg/ml | 2 ug/ml | 102 |
| α1-PI | 1 mg/ml | 30 ug/ml | 98 |

| -continued | | | |
|---|---|---|---|
| Inhibition of Amyloidin | | | |
| Inhibitor* | Stock conc. | Assay conc. | % Control Activity |
| α1-ACT | 1 mg/ml | 30 ug/ml | 121 |

*PMSF, phenylmethylsulfonyl fluoride; DFP, Diisopropyl-fluorophosphate; EDTA, ethylenediaminetetraacetic acid; 1,10-phen., 1,10-phenanthroline; calp. inh. II, calpain inhibitor II; α1-PI, α1-proteinase inhibitor; α1-ACT, α1-antichymotrypsin.

Calpain inhibitor-II or E-64 (both strong inhibitors of the $Ca^{++}$-dependent cysteine protease, calpain), had no inhibitory effect on amyloidin. 1,10-phenanthroline and phosphoramidon, both strong inhibitors of metalloproteases, were only weakly inhibitory (25% inhibition). Neither α-1-proteinase inhibitor or α-1-antichymotrypsin, two general plasma serine proteinase inhibitors, had any inhibitory effect on amyloidin, nor did aprotinin, the bovine Kunitz trypsin inhibitor.

Example 3

Structural Characterization

A. Amyloidin

To obtain sequence information, approximately 300 picomoles of amyloidin purified from human brain tissue (Example 1) were electrophoresed on a 7.5% acrylamide gel using SDS-PAGE, and the protein band was visualized with Poinceau Red (stock solution from Sigma diluted 1:10 with water).

The band was excised from the gel and minced into small pieces with a clean razor blade. 30 picomoles of Lys-C endopeptidase (Boehringer Mannheim) in 100 ul 50 mM Tris-HCl, pH 8.5, 1 mM EDTA, was then added to the protein, and incubated overnight. The gel pieces were repeatedly extracted with 10 mM ammonium bicarbonate in acetonitrile (5×100 ul), the washings combined and dried. The dried gel samples were then taken up in 50 ul 0.1% TFA, and injected into a 0.2 cm×15 cm Vydac C18 micropore column, and eluted with a linear gradient of 0-60% acetonitrile over 60 min. The three peaks that were deemed most pure were then sequenced to completion or to whatever was practical on an Applied Biosystems 470A automated protein sequencer, with online PTH analysis, using the programs supplied by the manufacturer.

The three most prominent peaks were sequenced and are provided below:

$H_2N$-Arg-Val-Tyr-Asp-Gln-Val-Gly-Thr-Gln-Glu-phe-Glu-Asp-Val-Ser-Tyr-Glu-Ser-Thr-Leu-Lys-COOH (Seq. ID No.2);

$H_2N$-Val-Asp-Gln-Ala-Leu-His-Thr-Gln-Thr-Asp-Ala-Asp-Pro-Ala-Glu-Glu-Tyr-Ala-Arg-Leu-Cys-Gln-Glu-Ile-Leu-Gly-Val-Pro-Ala-Thr (Seq. ID No:3); and $H_2N$-Glu-Tyr-Phe-Pro-Val-Gln-Val-Val-Thr-His-Gly-Leu-Leu-Gly-Ile-Tyr-Gln-Glu-Leu-Leu-Gly-Leu-Ala-Phe-His-His (Seq. ID No:4).

Direct attempts at sequencing the 80,000 MW band, by transferring to Immobilon membranes (Millipore) were unsuccessful, which indicated a probable blocked N-terminus.

Example 4

Substrate Specificity

The ability of amyloidin to cleave short peptide-based para-nitroanilide substrates was tested by incubating 10 ul of a 20 mM stock of peptide p-NA substrate with 25 ul of enzyme, 20 ul of 100 mM $CaCl_2$, 40 ul of 1M Tris-HCl, pH 7.5, and 105 ul water, in 96-well microtiter plates, and monitoring for increase in absorbance at 405 nm, in a Molecular Devices Vmax Kinetic Microplate Reader. The results are provided below. No measurable increase in $A_{405}$ was detected, even after incubations up to 2 hours. Thus, amyloidin does not appear to cleave the pNA substrates tested, including one which is derived from the APP592–601 sequence.

| Substrate* | Amyloidin |
| --- | --- |
| Suc-AAPM-pNA | 0 |
| MeS-AAPV-pNA | 0 |
| Suc-AAPF-pNA | 0 |
| Ac-AD-pNA | 0 |
| Boc-AAd-Pna | 0 |
| Z-AA-pNA | 0 |
| Z-RR-pNA | 0 |
| Z-RK-pNA | 0 |
| Ac-EVKM-PNA | 0 |

*alanyl-alanyl-prolyl-methionyl–.; MeS-AAPV-, Methoxysuccinyl-alanyl-alanyl-prolyl-valyl-; Suc-AAPF-, Succinyl-alanyl-alanyl-prolyl-phenylalanyl-; Ac-AD-, Acetyl-alanyl-aspartyl-; Boc-AAD-, Butyloxycarbonyl-alanyl-alanyl-aspartyl-; Z-AA-, benzyloxycarbonyl-alanyl-alanyl-; Z-RR-, benzyloxycarbonyl- arginyl-arginyl-; Z-RK-, benzyloxycarbonyl-arginyl-lysyl-; Ac-EVKM-, acetyl-glutamyl-valyl-lysyl-methinyl-pNA; pNA-, para-nitroaniline Amyloidin does not appear to cleave oligopeptide para-nitroanilide substrates, including one based on the APP sequence after which it cleaves in the APP592–601 peptide.

Various peptides were purchased from Bachem (Torrance, Calif.) and incubated with the human amyloidin protease using the conditions described in Example 1D. Cleavage products were isolated by reverse-phase HPLC, and subjected to amino acid analysis to determine site(s) of cleavage. The following table show the results obtained with amyloidin protease compared to reported site(s) of cleavage by Pz-peptidase.

| Substrate | Cleavage Products | |
| --- | --- | --- |
| Bradykinin | ArgProProGlyPhe | SerProPheArg |
| Neurotensin | GluLeuTyrGluAspLysProArg | ArgProTyrIleLeu |
| LH-RH | GluHis   TrpSerTyr | GlyLeuArgProGlyNH2 |
|  |  (minor) |  |
| Dynorphin A108 | TyrGlyGlyPheLeu | ArgArgIle |
|  |  | (minor) |

The spaces indicate cleavage sites of Pz-peptidase reported by Barrett (1990), supra. Underlined peptides are those identified following cleavage by the amyloidin of the present invention.

Example 5

Subsite Requirements

In order to test the subsite requirements of amyloidin in the APP592–601 cleavage assay, analogs of this peptide substrate were synthesized.

A. Chemical Synthesis of (N-acetyl)-APP (592–601) CONH2 analogs

The peptide corresponding to residues 592 to 601 of the 695 APP was synthesized on the Applied Biosystems Model 430A Peptide Synthesizer using the t-boc methodology. All boc-amino acids and synthesis reagents were purchased from Applied Biosystems Inc., and the amino acid side chain protecting groups are as follows: Arg(TOS), Asp(OBzl), Lys(2ClZ), and Ser-(OBzl). Ala, Met, Phe, Gln, Nleu and Val were used with no side chain protecting group. [(TOS)—tosyl, (OBzl)—O benzyl, (2ClZ)—2,6-dichlorocarbobenzoxy]. The software for controlling the synthetic cycle was designed specifically for making long chain peptides and peptides with sequence specific coupling difficulties. The general cycle is as follows: boc deprotection, neutralization; amino acid activation, 1st coupling (in $CH_2Cl_2$), neutralization; amino acid activation; 2nd coupling (in dimethylformamide), neutralization; and finally acetic anhydride capping.

Boc-amino acids were activated as preformed symmetric anhydrides by addition of 0.5 equivalents of N,N-dicyclohexylcarbodiimide (DCC) with the exception of boc-Arg(TOS) which was activated to its corresponding HOBT-ester by addition of 1 equivalent of 1-hydroxybenzotriazole and 1 equivalent of DCC. After the second coupling of each amino acid, any uncoupled amine remaining was capped by addition of acetic anhydride in $CH_2Cl_2$ plus a catalytic amount of diisopropylethylamine (DIEA). The capping step is to prevent synthesis of deleted peptide sequences which are often difficult to separate from the target peptide during purification.

After addition of the N-terminal amino acid, the boc group was removed using 50% (TFA) in $CH_2Cl_2$ and neutralized with a solution of 10% DIEA in $CH_2Cl_2$. The exposed primary amine of the N-terminal amino acid was then acetylated using the same protocol using the capping step.

The solid support, p-methylbenzhydrilamine resin, was purchased from Fisher Biotech. Treatment of the fully protected peptide resin with anhydrous HF, cleaved the peptide from the solid support, removed all the side chain protecting groups, and produced the crude peptide product as the C-terminal carboxy amide derivative.

The crude peptide was purified to >98.0% purity using preparative scale reverse phase chromatography on a Vydac, C18, 330A, 10um column with dimensions of 2.2 cm×25 cm in length. The crude peptide was dissolved and loaded onto the column in 5%, [0.1% TFA/CH3CN]/H2O and eluted using a linear gradient of 5% to 50% [B] over 135 minutes. ([B]=0.1% TFA/CH3CN).

The structural integrity of the purified peptide was assessed by analytical HPLC, amino acid composition analysis, and mass spectrometry.

Following synthesis and purification, the peptides were then incubated with amyloidin under conditions identical to those developed with APP592–601. The results are summarized below. The underlined residues designated changes from the native peptide sequence while the arrows indicate peptide cleavage sites.

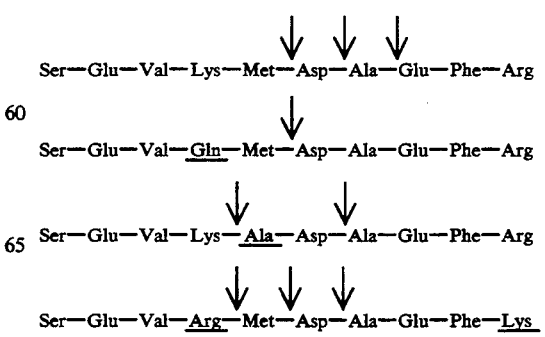

-continued

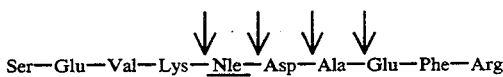

Ser—Glu—Val—Lys—Nle—Asp—Ala—Glu—Phe—Arg

With the exception of the analog in which Lys595 was replaced with a Gln, amyloidin cleaved at multiple sites, which differed from peptide to peptide. The replacement of Met596 by Ala resulted in loss of cleavage at this site, but cleavage shifted to the Lys595-Ala596 bond. In the Gln595 analog, all the cleavage by amyloidin was at the Met-Asp bond.

While amyloidin has been demonstrated to make the relevant cleavage at the Met-Asp bond of synthetic amyloidin substrates, under certain preliminary conditions tested, the protease did not cleave the full-length protein (APP) produced by baculovirus cells transformed with the gene encoding APP. However, this does not preclude the involvement of this enzyme in the processing of APP as amyloidin may be only one of several enzymes whose combined activity is necessary for the generation of the β-peptide from APP.

Example 6

Purification of Clipsin/RMCP I

The procedure to isolate RMCP I was adapted exactly from that described by Nelson & Siman (1990), supra. However, after the final extraction of the membrane pellets with 50 mM HEPES, pH 7.5, 1M MgCl$_2$, and 0.1% Brij 35, the soluble extract was not further dialyzed, but loaded onto an immobilized soybean trypsin inhibitor column. This protocol and the subsequent steps were adapted from that taught from the purification of RMCP I described in Woodburg, et al, supra.

The soybean trypsin inhibitor column was prepared as follows: 15 mg of soybean trypsin inhibitor (Sigma Chemicals) was dissolved in 10 ml of 0.1M sodium bicarbonate, pH 8.5, and mixed with 3 g of washed activated CH-Sepharose (Sigma) for 2 h end-over-end in a plastic tube. The gel slurry was then filtered over a coarse sintered glass funnel, and extensively washed with alternating buffers, 0.1M formate, pH 3, and 0.2M Tris-HCl, pH 8. The washed gel was re-suspended in 0.2M Tris, pH 8, then equilibrated with 50 volumes of the same buffer after loading in a small glass column. The gel was then equilibrated with 50 mM HEPES, pH 7.5, 1M MgCl$_2$, and 0.1% Brij 35. The RMCP I extract was then loaded onto the column, and the flow-through material re-applied three times. (Measurement of Suc-Ala-Ala-Pro-Phe-pNA hydrolysis, which was used by Nelson & Siman to assay for "clipsin" activity, indicated that 95% of this activity had bound to the matrix.) The column was then washed with 5 volumes of the loading buffer, then eluted with 10 ml of 25 mM formate, pH 3, 0.1 mg/ml bovine serum albumin. The eluate was collected into an equal volume of 0.2M ammonium bicarbonate, pH 8.6, with 0.1 mg/ml BSA. This pool was diluted 1:1 with distilled water and treated with 1 g of reagent grade barium sulfate (Aldrich) for 30 min on ice. The supernatant was decanted and the pellet washed with 5 ml of 10 mM Tris, pH 8. The pellet was extracted with 2 ml of 20 mM Tris, pH 8 and 1M NaCl. This extract was assayed for both Suc-Ala-Ala-Pro-Phe-pNA hydrolysing activity, as well as APP592–601 cleaving activity. APP592–601 was cleaved at the Met-Asp bond, and this protease activity was completely inhibited by pre-treating the protease aliquot with 200 ng of α$_1$-antichymotrypsin, which had been shown to be a strong inhibitor of RMCP I. This pre-treatment also completely eliminated the measured Suc-Ala-Ala-Pro-Phe-pNA hydrolysing activity.

Incubation of 200 ng each of RMCP I and human skin chymase (HSC), obtained from Dr. Norman Schecter, University of Pennsylvania, with APP592–601 in the standard peptide cleavage assay also resulted in cleavage at the Met-Asp bond. Since the latter two enzymes are known to hydrolyze Suc-Ala-Ala-Pro-Phe-pNA, and are also inhibitable by α$_1$-antichymotrypsin, this suggested that RMCP I and HSC all belong to a second class of proteases, distinct from amyloidin, but also able to cleave the APP592–601 at the Met-Asp peptide bond.

Example 7

Production of Antibodies

Figure 3A:
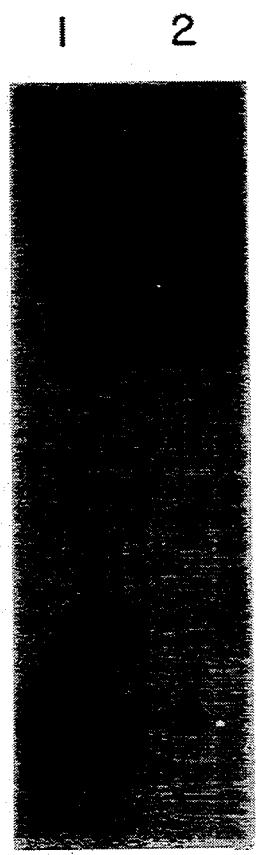
FIG. 3A and 3B are Western blot analyses of rabbit polyclonal antisera against an amyloidin protease synthetic peptide.
Figure 3B:
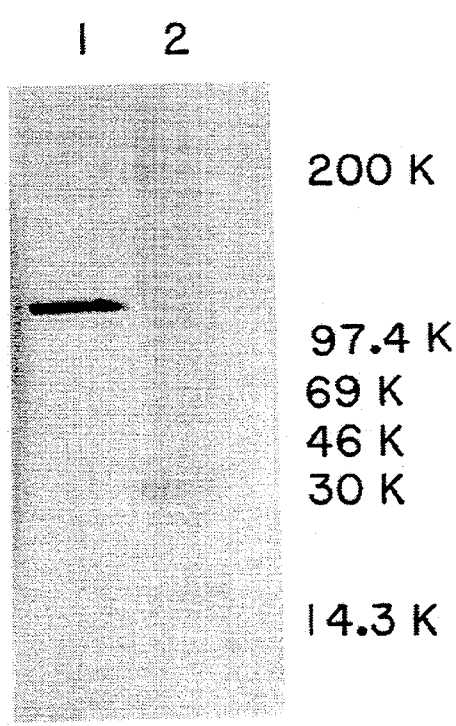

For the generation of antibodies to amyloidin, two approaches were taken. A peptide sequence corresponding to Seq. ID No: 2 obtained from structural analysis of amyloidin, but having a substituted Cys at the amino-terminus was synthesized by the standard synthesis methods described earlier. About 72 mg of the crude HF-cleaved peptide (Cys-Val-Tyr-Asp-Gln-Val-Gly-Thr-Gln-Glu-Phe-Glu-Asp-Val-Ser-Tyr-Glu-Ser-Thr-Leu-Lys) were conjugated to 12 mg of rabbit serum albumin (RSA), using Sulfo-MBS (Pierce, U.S.A.) in 50 mM potassium phosphate, pH 7 (Lerner, et al (1981) Proc Natl Acad Sci U.S.A. 78:3403–3407). The conjugation reaction was allowed to proceed for 20 min on ice, then immediately separated on a Sephadex G-10 column. The conjugated protein pool was sent to Josmin Laboratories (Berkeley, Calif.) for injection into rabbits. Briefly, primary immunization was done with 0.5 mg of conjugated RSA, followed by a first boost after three weeks. The first bleed obtained two weeks after the last of three weekly injections was tested by Western blot analysis for reaction against purified amyloidin. Strong reaction was obtained in the antiserum from one of the two rabbits injected, and this serum was further processed by isolating a crude IgG fraction by sodium sulfate fractionation. As shown in FIG. 3A and 3B, a Western blot using the IgG fraction diluted 1:500 as the primary antibody, the 80,000 dalton protein band in amyloidin is exclusively recognized. Lane 1 (FIG. 3A) shows pre-stained Bio-Rad low molecular weight markers and Lane 2 (FIG. 3B) shows Amersham Rainbow markers; Lane 2 (FIG. 3A) and Lane 1 (FIG. 3B) show the purified amyloidin.

In the second approach, 60 ug of purified amyloidin were electrophoresed on SDS-PAGE, and the 80,000 dalton amyloidin band visualized by Rapid Reversible Stain (Diversified Biotech). The protein band was excised with a razor blade, then destained according to the manufacturer's instructions. The gel strip was then cut into small pieces and homogenized with a small amount of phosphate buffered saline (PBS) and emulsified into a water-in-oil emulsion with Freund's complete adjuvant by repeated passage through an emulsifying needle. Aliquots (20 ug) of this were injected into three Balb/C mice. This procedure was repeated every other week, with the modification that subsequent emulsifications were done with Freund's incomplete adjuvant. The serum of each mouse was tested for reactivity against purified amyloidin by Western blot analysis after three injections. The mouse whose serum showed the strongest reactivity was further selected for fusion with myeloma cells to generate hybridomas producing antibodies against amyloidin. The hybridomas were generated by standard murine fusion procedures as described in ANTIBODIES: A Laboratory Manual by Harlow & Lane (Cold Spring Harbor Laboratories, 1988). Briefly, the immunized mouse was sacrificed and the spleen removed. Mixed splenocytes were obtained by pressing the spleen between frosted ends of glass slides. These were fused with SP2/0Ag14 plasmacytoma cells (ATCC No. CRL1581) at a fusion ratio of 1:3 in Dulbecco's modified Eagle's media (DMEM), supplemented with 20% fetal bovine serum (FBS), 2 mM glutamine, 15 mM HEPES and 0.1 mM hypoxanthine. Hybridomas were selected for by growing the cells in the presence of azaserine supplemented DMEM, augmented with hypoxanthine and 20% FBS. Hybridomas were screened for reactivity against purified human brain amyloidin using an ELISA. Positives were further tested in Western blots and the results are shown in FIG. 4. From this single source, 10 monoclonals have been generated which recognize purified amyloidin strongly on Western blots.

Example 8

Immunohistological Studies

Brain tissue from Alzheimer disease (AD) patients and age matched controls was immersion fixed in 4.0% paraformaldehyde in 0.1M phosphate buffer and cut into 40 µm sections on a sliding microtome. Sections were collected in 0.1M phosphate buffer and quenched for endogenous peroxidase activity for 20 minutes in 0.3% hydrogen peroxide and 0.5% Triton X-100 in 0.1M phosphate buffer. They were blocked for 1.0 hour in 5.0% milk in phosphate buffer and then incubated for 24 hours in the polyclonal antibody to amyloidin protease diluted 1:20 in 1.5% goat serum and phosphate buffer. As controls, some sections were incubated at the same concentration with preimmune sera from the rabbit producing the antibody and antibody adsorbed with the amyloidin peptide. They were then processed for immunocytochemistry using standard procedures for the goat anti rabbit IgG Vectastain ABC kit (Vector Laboratories). Brain tissue from rats transcardially perfused with 9.9% NaCl followed by PLP fixative was similarly processed. In addition, similar tissue from rat, AD and age matched control brains was embedded in paraffin and cut into 8 µm sections. These sections were baked for 1.0-3.0 hours and hydrated by passing the sections for 3.0 minutes each in three changes of xylene, two changes of 100% ETOH, and one change each through 95%, 70%, 50% EtOH and dH2O). These were also routinely processed with the Vectastain ABC kit. To determine the efficacy of formic acid pretreatment, some of the paraffin embedded material was incubated with formic acid for 3.0 minutes following hydration.

In both normal and AD brains the antibody stained large neurons in layers III and IV, white matter astrocytes, and smooth muscle cells. In AD brains large reactive astrocytes were stained in the gray matter. This staining was not seen with preimmune sera and was blocked by adsorbing the antibody with the peptide antigen. In rat brain, a number of astrocytes in the hippocampus were labeled; no neurons were labeled.

In paraffin embedded AD sections without formic acid pretreatment only smooth muscle cells and a few, presumably reactive, astrocytes in the gray matter were labeled; no obvious pathology was stained. However after formic acid pretreatment, the predominant staining in the same brains was associated with AD pathology; dystrophic neurites, notably those forming neuritic plaques were labeled. Several large neurons were also labeled, however they were not found evenly distributed throughout the gray matter. Instead they were found in clusters, usually in layer V. Smooth muscle cells were also labeled.

In rat paraffin embedded material, no cortical neurons were labeled before or after pretreatment with formic acid. Only smooth muscle cells were seen in cortical arterioles, little or no labeling was seen in the cerebellum. A few neurons were labeled in the midbrain.

In summary, the staining patterns of the polyclonal antibody against amyloidin protease indicate that it may be abundant in human brain cells and may be highly expressed in the cellular components underlying the pathology associated with Alzheimer's Disease. The reason why formic acid pretreatment changes the staining pattern in paraffin embedded in tissue is unclear; the compromised epitope may be altered or obscured in dystrophic versus normal cells and neurites. The lack of neuronal staining in the rat is interesting and may signify a difference in degradation products between the two species.

Example 9

Cloning of the Gene Encoding Human Amyloidin

Total RNA was extracted from normal human brain (patient ID 87-5); superior temporal gyrus and a human embryonic kidney cell line; 293 (ATCC No. CRL1573). As shown in Example 1, human brain homogenates have amyloidin activity. Similarly, 293 cell extracts were shown to have amyloidin activity and therefore cDNA made from this RNA would be a preferred template for amyloidin sequence identification.

Complementary DNA was generated using random hexamers. PCR primers were designed to give the longest PCR product of region III (Seq. ID No:4). The sequence of the PCR primers (EJ-87 and EJ-88) were based on Lathe's rules ((1985) *J Mol Biol* 183:1-12) although degenerate primers did work also (EJ-91, EJ-92 and EJ-93).

```
EJ-87: 5' TCGAATTC AAG GAG TAC TTC CCT GT 3' (Seq ID No:  7
EJ-88: 5' CAAAGCTT TG GAA GGC CAG GCC CAG 3' (Seq ID No:  8)
EJ-89: 5' CAT GGC CTG CTG GGC ATC TAC CAG GAG 3' (Seq ID No:  9)
EJ-91: 5' TCGAATTC AAR GAR TAY TTY CCN GT 3' (Seq ID No:  10)
EJ-92: 5' CAAAGCTT RTG RTT NGC NAG NCC 3' (Seq ID No:  11)
EJ-93: 5' CAAAGCTT RTG RTT NGC YAA NCC 3' (Seq ID No:  12)
``` where N can be A, T, C or G; R can be A or G; and Y can be C or T.

PCR products were analyzed by Southern blot hybridization using internal probe EJ-89. PCR reactions were performed at 95° C.; 1 min denaturing, 42° C., 48° C. or 54° C.; 1 min annealing; 72° C., 1 min extension times for 35 cycles. A 93 bp product of the EJ-87/88 reaction that did hybridize with EJ-89 was excised from an analytical acrylamide gel and used as template for a re-PCR reaction. DNA sequencing was performed using EJ-87 and EJ-88 as primers as described by Smith, et al (1990) *Biotechniques* 9:51. A unique DNA sequence of approximately 40 base pairs was then provided for further cloning efforts.

This 40 base pairs of unique sequence, along with flanking sequence from the PCR oligos EJ-87 (Seq ID No:7) and EJ-88 (Seq ID No:8), were used to generate an oligo probe, designated 811 (Seq ID No:13) 5' AAG-GAGTACT TCCCTGTGCA GGTGGTCACG CACGGGCTGC TGGGCATCTA CCAG-GAGCTC CTGGGCCTGG CCTTC 3' to screen libraries for amyloidin clones.

Because this probe contains at least 40 contiguous base pairs of exact sequence, stringent conditions (55° C., 0.1× SSC wash) were used during screening; otherwise screening techniques were standard (see Sambrook, et al (1990)). This probe was used to screen a temporal cortex cDNA library (obtained from Stratagene, catalogue number 935205), and one clone (clone 19) was obtained. Partial sequence generated from clone 19 was used to design the following PCR oligos:

895 (Seq ID No:14) 5' GAAATGCACG
TGCCTGAG 3'

889 (Seq ID No:15) 5' CCAGGACATA
GTCGGCG 3' that were used to generate a double-stranded PCR probe from the 5' end of clone 19. Although the Stratagene library was screened with this probe (Seq ID No:16) 5' GAAATGCACG TGCCTGAGAC CAG-GAGGAAA GTGGAGGAGG CCTTCAACTG CCGGTGCAAG GAGGAGAACT GCGCTATCCT CAAGGAGCTG GTGACGCTGC GGGCCCAGAA GTCCCGCCTG CTGGGGTTCC ACACGCACGC CGACTATGTC CTGG 3', no clones containing the 5' end of the coding region of amyloidin were obtained.

Western analysis showed that HeLa cells also contain amyloidin. A standard HeLa cell random primed cDNA library in the lambda gt10 vector was provided by Dr. Bernhard Luscher (University of California, Berkeley). Commercially available HeLa cell cDNA libraries are available from Stratagene (catalogue number 936201) and Clontechh (catalogue number HL1022b). This library was screened with the same PCR probe generated from oligos 889 and 895 described above, and 30 positive clones were plaque purified. The amounts of 5' and 3' flanking sequences in all of the positive clones were estimated by PCR analysis using oligos homologous to the lambda vector sequences (from Clontech, catalogue number 5411-1) and either an oligo made to the 5' end of clone 19 (antisense strand; oligo 909; 5' ACTTTCCTCCTGGTCTCA 3') (Seq ID No:17) or to the 3' end of clone 19 (coding strand; oligo 905; 5' GGAGAAGCTCATTGAGTC 3') (Seq ID No:18). Sizing of the PCR products was done by agarose electrophoresis, and those clones with the most flanking sequences were chosen for sequence analysis. These clones were cut out of the lambda vector and subcloned into M13 for sequencing. Two clones, clones cHL57 and cHL53, which together span the entire coding region of amyloidin, were chosen for complete sequence analysis.

The coding region of human amyloidin is provided as Seq ID No:6. The complete sequence of the human amyloidin gene was obtained by sequencing two clones: clone cHL57 provided the nucleotide sequence encoding amino acid residues 1 through 480, with Met1 of Seq ID No:5 being the putative initiation codon; clone cHL53 provided the nucleotide sequence encoding amino acid residues 56 thorough the stop condon of the amyloidin protease. Examination of the nucleotide sequence reveals that there is no clear hydrophobic leader sequence as would be expected for a secreted or membrane-bound protein. This is similar to that found by Pierotti, et al (1990), supra for the rat Pz-peptidase. However, the human amyloidin sequence, in contrast to the rat Pz-peptidase sequence, contains approximately 132 base pairs of additional coding DNA, and therefore codes for an enzyme having approximately 44 additional amino acid residues at the carboxy-terminus. The open reading frame of the cDNA encoding human amyloidin is composed of 2070 nucleotides, including the stop codon (Seq ID No:6), encoding a protein with 689 amino acids residues (Seq ID No:5). Like other members of the family of zinc-dependent metallopeptidases, human amyloidin contains the typical amino acid sequence at and around the active site that is represented by the motif Xaa-His-Glu-Phe-Gly-His-Xaa, in which the two histidine residues coordinate the $Zn^{2+}$ in the active center and the glutamate is involved in bond-breaking process.

---

We claim:

1. A method for the identification of an inhibitor of an amyloidin metalloprotease of approximately 80,000 daltons, said method comprising:
   a) combining the metalloprotease with a potential inhibitor under conditions sufficient to form a mixture comprising a complex of the metalloprotease and the potential inhibitor;
   b) introducing the mixture to an amyloid-like substrate under conditions sufficient to cleave the Met-Asp bond in said substrate; and
   c) monitoring whether cleavage of the Met-Asp bond in the substrate has occurred, wherein a potential inhibitor that inhibits the cleavage of the Met-Asp bond is an inhibitor.

2. The method of claim 1, wherein the metalloprotease and the potential inhibitor are initially combined in the presence of the substrate.

3. A method for the identification of an inhibitor of a metalloprotease of approximately 80,000 daltons capable of cleaving an endopeptidic Met-Asp bond in an amyloid-like substrate, said method comprising:
   a) combining the metalloprotease with a potential inhibitor and an amyloid-like substrate under conditions sufficient to cleave the Met-Asp bond on the amyloid-like substrate; and b) monitoring whether cleavage of the Met-Asp bond in the substrate has occurred.

4. The method of claim 3, wherein the metalloprotease is human amyloidin protease.

5. The method of claim 3, wherein the amyloid-like substrate corresponds substantially to the peptide:

acetyl-Ser-Glu-Val-Xaa$_4$-Met-Asp-Ala-Glu-Phe-Arg wherein Xaa$_4$ is Gln or Lys (SEQ. ID. NO. 1).

6. The method of claim 3 wherein the amyloid-like substrate is a fragment of the amyloid precursor protein.

7. The method of claim 3, wherein the amyloid-like substrate is labeled.

8. The method of claim 7, wherein the label comprises a signal means and a capture means.

9. The method of claim 8, wherein the capture means is a specific binding partner.

10. The method of claim 8, wherein the signal means is capable of emitting radiation.

11. A method for the identification of an inhibitor of a metalloprotease of approximately 80,000 daltons capable of cleaving an endopeptidic Nle-Asp bond is an amyloid-like substrate, wherein the amyloid-like substrate corresponds substantially to the peptide:

acetyl-Ser-Glu-Val-Xaa$_4$-Nle-Asp-Ala-Glu-Phe-Arg wherein Xaa$_4$ is Gln or Lys (SEQ. ID. NO. 1), said method comprising:

a) combining the metalloprotease with a potential inhibitor under conditions sufficient to cleave the Nle-Asp bond of the amyloid-like substrate; and b) monitoring whether cleavage of the Nle-Asp bond in the substrate has occurred. Suc-AAPM-, Succinyl-alanyl-alanyl-prolyl-methionyl

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( i x ) FEATURE:
  ( A ) NAME/KEY: Modified-site
  ( B ) LOCATION: 4
  ( D ) OTHER INFORMATION: /label=Xaa4
    / note="Xaa4 can be either Gln or Lys"

( i x ) FEATURE:
  ( A ) NAME/KEY: Modified-site
  ( B ) LOCATION: 5
  ( D ) OTHER INFORMATION: /label=Xaa5
    / note="Xaa5 can be either Met or Nle"

( x i ) SEQUENCE DESCRIPTION: SEQ ID NO:1:

```
Ser Glu Val Xaa Xaa Asp Ala Glu Phe Arg
1               5                   10
```

( 2 ) INFORMATION FOR SEQ ID NO:2:

( i ) SEQUENCE CHARACTERISTICS:
  ( A ) LENGTH: 21 amino acids
  ( B ) TYPE: amino acid
  ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

```
Arg Val Tyr Asp Gln Val Gly Thr Gln Glu Phe Glu Asp Val Ser Tyr
1               5                   10                  15

Glu Ser Thr Leu Lys
            20
```

( 2 ) INFORMATION FOR SEQ ID NO:3:

( i ) SEQUENCE CHARACTERISTICS:
  ( A ) LENGTH: 30 amino acids
  ( B ) TYPE: amino acid
  ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

```
Val Asp Gln Ala Leu His Thr Gln Thr Asp Ala Asp Pro Ala Glu Glu
1               5                   10                  15

Tyr Ala Arg Leu Cys Gln Glu Ile Leu Gly Val Pro Ala Thr
            20              25                  30
```

( 2 ) INFORMATION FOR SEQ ID NO:4:

( i ) SEQUENCE CHARACTERISTICS:
  ( A ) LENGTH: 26 amino acids
  ( B ) TYPE: amino acid
  ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:4:

```
Glu Tyr Phe Pro Val Gln Val Val Thr His Gly Leu Leu Gly Ile Tyr
1               5                   10                  15

Gln Glu Leu Leu Gly Leu Ala Phe His His
            20                  25
```

( 2 ) INFORMATION FOR SEQ ID NO:5:

( i ) SEQUENCE CHARACTERISTICS:
        ( A ) LENGTH: 689 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

```
Met Lys Pro Pro Ala Ala Cys Ala Gly Asp Met Ala Asp Ala Ala Ser
1               5                   10                  15

Pro Cys Ser Val Val Asn Asp Leu Arg Trp Asp Leu Ser Ala Gln Gln
            20                  25                  30

Ile Glu Glu Arg Thr Arg Glu Leu Ile Glu Gln Thr Lys Arg Val Tyr
            35                  40                  45

Asp Gln Val Gly Thr Gln Glu Phe Glu Asp Val Ser Tyr Glu Ser Thr
        50                  55                  60

Leu Lys Ala Leu Ala Asp Val Glu Val Thr Tyr Thr Val Gln Arg Asn
65                  70                  75                  80

Ile Leu Asp Phe Pro Gln His Val Ser Pro Ser Lys Asp Ile Arg Thr
                85                  90                  95

Ala Ser Thr Glu Ala Asp Lys Lys Leu Ser Glu Phe Asp Val Glu Met
            100                 105                 110

Ser Met Arg Glu Asp Val Tyr Gln Arg Ile Val Trp Leu Gln Glu Lys
        115                 120                 125

Val Gln Lys Asp Ser Leu Arg Pro Glu Ala Ala Arg Tyr Leu Glu Arg
    130                 135                 140

Leu Ile Lys Leu Gly Arg Arg Asn Gly Leu His Leu Pro Arg Glu Thr
145                 150                 155                 160

Gln Glu Asn Ile Lys Arg Ile Lys Lys Leu Ser Leu Leu Cys Ile
                165                 170                 175

Asp Phe Asn Lys Asn Leu Asn Glu Asp Thr Thr Phe Leu Pro Phe Thr
            180                 185                 190

Leu Gln Glu Leu Gly Gly Leu Pro Glu Asp Phe Leu Asn Ser Leu Glu
        195                 200                 205

Lys Met Glu Asp Gly Lys Leu Lys Val Thr Leu Lys Tyr Pro His Tyr
    210                 215                 220

Phe Pro Leu Leu Lys Lys Cys His Val Pro Glu Thr Arg Arg Lys Val
225                 230                 235                 240

Glu Glu Ala Phe Asn Cys Arg Cys Lys Glu Glu Asn Cys Ala Ile Leu
                245                 250                 255

Lys Glu Leu Val Thr Leu Arg Ala Gln Lys Ser Arg Leu Leu Gly Phe
            260                 265                 270

His Thr His Ala Asp Tyr Val Leu Glu Met Asn Met Ala Lys Thr Ser
        275                 280                 285

Gln Thr Val Ala Thr Phe Leu Asp Glu Leu Ala Gln Lys Leu Lys Pro
    290                 295                 300

Leu Gly Glu Gln Glu Arg Ala Val Ile Leu Glu Leu Lys Arg Ala Glu
```

|  305 | | | | | 310 | | | | | 315 | | | | | 320 |
|---|---|---|---|---|---|---|---|---|---|---|---|---|---|---|---|
| Cys | Glu | Arg | Arg | Gly | Leu | Pro | Phe | Asp | Gly | Arg | Ile | Arg | Ala | Trp | Asp |
| | | | | 325 | | | | | 330 | | | | | 335 | |
| Met | Arg | Tyr | Tyr | Met | Asn | Gln | Val | Glu | Thr | Arg | Tyr | Cys | Val | Asp | |
| | | | 340 | | | | | 345 | | | | | 350 | | |
| Gln | Asn | Leu | Leu | Lys | Glu | Tyr | Phe | Pro | Val | Gln | Val | Val | Thr | His | Gly |
| | | | 355 | | | | | 360 | | | | | 365 | | |
| Leu | Leu | Gly | Ile | Tyr | Gln | Glu | Leu | Leu | Gly | Leu | Ala | Phe | His | His | Glu |
| | | | 370 | | | | | 375 | | | | | 380 | | |
| Glu | Gly | Ala | Ser | Ala | Trp | His | Glu | Asp | Val | Arg | Leu | Tyr | Thr | Ala | Arg |
| 385 | | | | | 390 | | | | | 395 | | | | | 400 |
| Asp | Ala | Ala | Ser | Gly | Glu | Val | Val | Gly | Lys | Phe | Tyr | Leu | Asp | Leu | Tyr |
| | | | | 405 | | | | | 410 | | | | | 415 | |
| Pro | Arg | Glu | Gly | Lys | Tyr | Gly | His | Ala | Ala | Cys | Phe | Gly | Leu | Gln | Pro |
| | | | | 420 | | | | | 425 | | | | | 430 | |
| Gly | Cys | Leu | Arg | Gln | Asp | Gly | Ser | Arg | Gln | Ile | Ala | Ile | Ala | Ala | Met |
| | | | 435 | | | | | 440 | | | | | 445 | | |
| Val | Ala | Asn | Phe | Thr | Lys | Pro | Thr | Ala | Asp | Ala | Pro | Ser | Leu | Leu | Gln |
| | 450 | | | | | 455 | | | | | 460 | | | | |
| His | Asp | Glu | Val | Glu | Thr | Tyr | Phe | His | Glu | Phe | Gly | His | Val | Met | His |
| 465 | | | | | 470 | | | | | 475 | | | | | 480 |
| Gln | Leu | Cys | Ser | Gln | Ala | Glu | Phe | Ala | Met | Phe | Ser | Gly | Thr | His | Val |
| | | | | 485 | | | | | 490 | | | | | 495 | |
| Glu | Arg | Asp | Phe | Val | Glu | Ala | Pro | Ser | Gln | Met | Leu | Glu | Asn | Trp | Val |
| | | | 500 | | | | | 505 | | | | | 510 | | |
| Trp | Glu | Gln | Glu | Pro | Leu | Leu | Arg | Met | Ser | Arg | His | Tyr | Arg | Thr | Gly |
| | | | 515 | | | | | 520 | | | | | 525 | | |
| Ser | Ala | Val | Pro | Arg | Glu | Leu | Leu | Glu | Lys | Leu | Ile | Glu | Ser | Arg | Gln |
| | | 530 | | | | | 535 | | | | | 540 | | | |
| Ala | Asn | Thr | Gly | Leu | Phe | Ser | Leu | Arg | Gln | Ile | Val | Leu | Ala | Lys | Val |
| 545 | | | | | 550 | | | | | 555 | | | | | 560 |
| Asp | Gln | Ala | Leu | His | Thr | Gln | Thr | Asp | Ala | Asp | Pro | Ala | Glu | Glu | Tyr |
| | | | | 565 | | | | | 570 | | | | | 575 | |
| Ala | Arg | Leu | Cys | Gln | Glu | Ile | Leu | Gly | Val | Pro | Ala | Thr | Pro | Gly | Thr |
| | | | | 580 | | | | | 585 | | | | | 590 | |
| Asn | Met | Pro | Ala | Thr | Phe | Gly | His | Leu | Ala | Gly | Gly | Tyr | Asp | Ala | Gln |
| | | | 595 | | | | | 600 | | | | | 605 | | |
| Tyr | Tyr | Gly | Tyr | Leu | Trp | Ser | Glu | Val | Tyr | Ser | Met | Asp | Met | Phe | His |
| | | | 610 | | | | | 615 | | | | | 620 | | |
| Thr | Arg | Phe | Lys | Gln | Glu | Gly | Val | Leu | Asn | Ser | Lys | Val | Gly | Met | Asp |
| 625 | | | | | 630 | | | | | 635 | | | | | 640 |
| Tyr | Arg | Ser | Cys | Ile | Leu | Arg | Pro | Gly | Gly | Ser | Glu | Asp | Ala | Ser | Ala |
| | | | | 645 | | | | | 650 | | | | | 655 | |
| Met | Leu | Arg | Arg | Phe | Leu | Gly | Arg | Asp | Pro | Lys | Gln | Asp | Ala | Phe | Leu |
| | | | 660 | | | | | 665 | | | | | 670 | | |
| Leu | Ser | Lys | Gly | Leu | Gln | Val | Gly | Gly | Cys | Glu | Pro | Glu | Pro | Gln | Val |
| | | | 675 | | | | | 680 | | | | | 685 | | |
| Cys | | | | | | | | | | | | | | | |

( 2 ) INFORMATION FOR SEQ ID NO:6:

( i ) SEQUENCE CHARACTERISTICS:
( A ) LENGTH: 2070 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

| | | | | | |
|---|---|---|---|---|---|
| ATGAAGCCCC | CCGCAGCCTG | TGCAGGAGAC | ATGGCGGACG | CAGCATCTCC | GTGCTCTGTG | 60 |
| GTAAACGACC | TGCGGTGGGA | CCTGAGTGCC | CAGCAGATAG | AGGAGCGCAC | CAGGGAGCTC | 120 |
| ATCGAGCAGA | CCAAGCGCGT | GTATGACCAG | GTTGGCACCC | AGGAGTTTGA | GGACGTGTCC | 180 |
| TACGAGAGCA | CGCTCAAGGC | GCTGGCCGAT | GTGGAGGTCA | CCTACACAGT | TCAGAGGAAT | 240 |
| ATCCTTGACT | TCCCCCAGCA | TGTTTCCCCC | TCCAAGGACA | TCCGGACAGC | CAGCACAGAG | 300 |
| GCCGACAAGA | AGCTCTCTGA | GTTCGACGTG | GAGATGAGCA | TGAGGGAGGA | CGTGTACCAG | 360 |
| AGGATCGTGT | GGCTCCAGGA | GAAAGTTCAG | AAGGACTCAC | TGAGGCCCGA | GGCTGCGCGG | 420 |
| TACCTGGAGC | GGCTAATCAA | GCTGGGCCGG | AGAAATGGGC | TTCACCTCCC | CAGAGAGACT | 480 |
| CAGGAAAACA | TCAAACGCAT | CAAGAAGAAG | CTGAGCCTTC | TGTGCATCGA | CTTCAACAAG | 540 |
| AACCTGAACG | AGGACACGAC | CTTCCTGCCC | TTCACGCTCC | AGGAGCTAGG | AGGGCTCCCC | 600 |
| GAGGACTTTC | TGAACTCCCT | GGAGAAGATG | GAGGACGGCA | AGTTGAAGGT | CACCCTCAAG | 660 |
| TACCCCCATT | ACTTCCCCCT | CCTGAAGAAA | TGCCACGTGC | CTGAGACCAG | GAGGAAAGTG | 720 |
| GAGGAGGCCT | TCAACTGCCG | GTGCAAGGAG | GAGAACTGCG | CTATCCTCAA | GGAGCTGGTG | 780 |
| ACGCTGCGGG | CCCAGAAGTC | CCGCCTGCTG | GGGTTCCACA | CGCACGCCGA | CTATGTCCTG | 840 |
| GAGATGAACA | TGGCCAAGAC | CAGCCAGACC | GTGGCCACCT | TCCTAGATGA | GCTGGCGCAG | 900 |
| AAGCTGAAGC | CCCTGGGGGA | GCAGGAGCGT | GCGGTGATTC | TGGAGCTGAA | GCGTGCGGAG | 960 |
| TGCGAGCGCC | GGGGCCTGCC | CTTCGACGGC | CGCATCCGTG | CCTGGGACAT | GCGCTACTAC | 1020 |
| ATGAACCAGG | TGGAGGAGAC | GCGCTACTGC | GTGGACCAGA | ACCTGCTCAA | GGAGTACTTC | 1080 |
| CCCGTGCAGG | TGGTCACGCA | CGGGCTGCTG | GGCATCTACC | AGGAGCTCCT | GGGGCTGGCC | 1140 |
| TTCCACCACG | AGGAGGGCGC | CAGTGCCTGG | CATGAGGACG | TGCGGCTCTA | CACCGCGAGG | 1200 |
| GACGCGGCCT | CGGGGGAGGT | GGTCGGCAAG | TTCTACCTGG | ACCTGTACCC | GCGGGAAGGA | 1260 |
| AAGTACGGGC | ACGCGGCCTG | CTTTGGCCTG | CAGCCCGGCT | GCCTGCGGCA | GGATGGGAGC | 1320 |
| CGCCAGATCG | CCATCGCGGC | CATGGTGGCC | AACTTCACCA | AGCCCACAGC | CGACGCGCCC | 1380 |
| TCGCTGCTGC | AGCATGACGA | GGTGGAGACC | TACTTCCATG | AGTTTGGCCA | CGTGATGCAC | 1440 |
| CAGCTCTGCT | CCCAGGCGGA | GTTCGCCATG | TTCAGCGGGA | CCCACGTGGA | GCGGGACTTT | 1500 |
| GTGGAGGCGC | CGTCGCAGAT | GCTGGAGAAC | TGGGTGTGGG | AGCAGGAGCC | GCTGCTGCGG | 1560 |
| ATGTCGCGGC | ACTACCGCAC | AGGCAGCGCC | GTGCCCCGGG | AGCTCCTGGA | GAAGCTCATT | 1620 |
| GAGTCCCGGC | AGGCCAACAC | AGGCCTCTTC | AGCCTGCGCC | AGATCGTCCT | CGCCAAGGTG | 1680 |
| GACCAGGCCC | TGCACACGCA | GACGGACGCA | GACCCCGCCG | AGGAGTATGC | GCGGCTCTGC | 1740 |
| CAGGAGATCC | TCGGGGTCCC | GGCCACGCCA | GGAACCAACA | TGCCTGCAAC | CTTCGGCCAT | 1800 |
| CTGGCAGGTG | GCTACGACGC | CCAGTACTAC | GGGTACCTGT | GGAGCGAGGT | GTATTCCATG | 1860 |
| GACATGTTCC | ACACGCGCTT | CAAGCAGGAG | GGTGTCCTGA | CAGCAAGGT | TGGCATGGAT | 1920 |
| TACAGAAGCT | GCATCCTGAG | ACCCGGCGGT | TCCGAGGATG | CCAGCGCCAT | GCTGAGGCGC | 1980 |
| TTCCTGGGCC | GTGACCCCAA | GCAGGACGCC | TTCCTCCTGA | GCAAGGGGCT | GCAGGTCGGG | 2040 |
| GGCTGCGAGC | CCGAGCCGCA | GGTCTGCTGA | | | | 2070 |

( 2 ) INFORMATION FOR SEQ ID NO:7:

( i ) SEQUENCE CHARACTERISTICS:

(A) LENGTH: 25 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

TCGAATTCAA GGAGTACTTC CCTGT 25

(2) INFORMATION FOR SEQ ID NO:8:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:8:

CAAACGTTTG GAAGGCCAGG CCCAG 25

(2) INFORMATION FOR SEQ ID NO:9:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

CATGGCCTGC TGGGCATCTA CCAGGAG 27

(2) INFORMATION FOR SEQ ID NO:10:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

TCGAATTCAA RGARTAYTTY CCNGT 25

(2) INFORMATION FOR SEQ ID NO:11:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA ( i i i ) HYPOTHETICAL: NO ( i v ) ANTI-SENSE: YES ( x i ) SEQUENCE DESCRIPTION: SEQ ID NO:11:

CAAAGCTTRT GRTTNGCNAG NCC    23

( 2 ) INFORMATION FOR SEQ ID NO:12:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:12:

CAAAGCTTRT GRTTNGCYAA NCC    23

( 2 ) INFORMATION FOR SEQ ID NO:13:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: YES ( i v ) ANTI-SENSE: NO ( x i ) SEQUENCE DESCRIPTION: SEQ ID NO:13:

AAGGAGTACT TCCCTGTGCA GGTGGTCACG CACGGGCTGC TGGGCATCTA CCAGGAGCTC    60

CTGGGCCTGG CCTTC    75

( 2 ) INFORMATION FOR SEQ ID NO:14:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

GAAATGCACG TGCCTGAG    18

( 2 ) INFORMATION FOR SEQ ID NO:15:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES (x i) SEQUENCE DESCRIPTION: SEQ ID NO:15:

CCAGGACATA GTCGGCG        17

(2) INFORMATION FOR SEQ ID NO:16:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:16:

GAAATGCACG TGCCTGAGAC CAGGAGGAAA GTGGAGGAGG CCTTCAACTG CCGGTGCAAG        60

CCGGTGCAAG GAGGAGAACT GCGCTATCCT CAAGGAGCTG GTGACGCTGC GGGCCCAGAA        120

GTCCCGCCTG CTGGGGTTCC ACACGCACGC CGACTATGTC CTGG        164

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:17:

ACTTTCCTCC TGGTCTCA        18

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

GGAGAAGCTC ATTGAGTC        18